(12) United States Patent
Holmgren et al.

(10) Patent No.: US 8,592,468 B2
(45) Date of Patent: Nov. 26, 2013

(54) BACTERIAL THIOREDOXIN REDUCTASE INHIBITORS AND METHODS FOR USE THEREOF

(75) Inventors: Arne Holmgren, Stockholm (SE); Jun Lu, Stockholm (SE); Alexios Vlamis-Gardikas, Stockholm (SE); Rong Zhao, Stockholm (SE); Karuppasamy Kandasamy, Stockholm (SE); Lars Engman, Uppsala (SE); Lars Engstrand, Stockholm (SE); Sven Hoffner, Stockholm (SE)

(73) Assignee: Thioredoxin Systems AB, Sollentuna (SE)

( * ) Notice: Subject to any disclaimer, the term of this patent is extended or adjusted under 35 U.S.C. 154(b) by 0 days.

(21) Appl. No.: 13/070,457

(22) Filed: Mar. 23, 2011

(65) Prior Publication Data
US 2011/0288130 A1 Nov. 24, 2011

Related U.S. Application Data

(63) Continuation of application No. 11/751,915, filed on May 22, 2007, now abandoned.

(60) Provisional application No. 60/802,480, filed on May 22, 2006.

(51) Int. Cl.
  *A61K 31/425* (2006.01)
(52) U.S. Cl.
  USPC .......................................................... 514/373
(58) Field of Classification Search
  USPC ........................................................... 514/373
  See application file for complete search history.

(56) References Cited

U.S. PATENT DOCUMENTS

2004/0058952 A1* 3/2004 Kajiwara ...................... 514/301

FOREIGN PATENT DOCUMENTS

JP 04077476 * 3/1992

OTHER PUBLICATIONS

CDC Knowledge about causes of peptic ulcer disease, 1997, http://wonder.cdc.gov/wonder/prevguid/m0049679/m0049679.asp#head001000000000000.*

(Continued)

*Primary Examiner* — Shengjun Wang
(74) *Attorney, Agent, or Firm* — Steven M. Hoffberg; Ostrolenk Faber LLP

(57) ABSTRACT

The mechanism of action of Ebselen differentiates between bacterial and mammalian thioredoxin reductase (TrxR). It displays fast oxidation of mammalian Trx and via the NADPH-TrxR catalyzed turnover of ebselen selenol with hydrogen peroxide, and therefore are mammalian antioxidants. Ebselen, and its diselenide, are strong competitive inhibitors of *E. coli* TrxR with $K_i$ of 0.14 μM and 0.46 μM, respectively. *E. coli* mutants lacking glutathione reductase or glutathione were much more sensitive to inhibition by ebselen. Since either glutaredoxin or thioredoxin systems are electron donors to ribonucleotide reductase, ebselen targets primarily glutathione and glutaredoxin-negative bacteria, a class which includes major pathogens. Ebselen, and similar compounds are therefore useful as antibacterial agents, even for multiresistant strains. Two major pathogenic bacteria, which previously had not been known to be sensitive to ebselen, *Mycobacterium tuberculosis* (tuberculosis) and *Helicobacter pylori* (stomach ulcer and cancer), were shown to be excellent targets. *Helicobacter pylori* was also sensitive to ebsulfur.

6 Claims, 22 Drawing Sheets

(56) References Cited

OTHER PUBLICATIONS

Beil et al. "Helicobacter pylori Reduces intracellular Glutathione in gastric epithelial cells," Digestive Diseases and Sciences, 2000, vol. 45, No. 9, pp. 1769-1773.*
translation of JP 04077476.*
Mueller et al. "A novel biologically active selenoorganic compound IV. protective glutathione-depedent effect of PZ 51(Ebselene) against ADP-Fe induced lipid peroxidation in isolated hepatocytes," Biochemical Pharmacology, 1985, vol. 34, No. 8, pp. 1185-1189.*
Fischer et al. "On Benzisothiazolones: " A Series with a wide range of bacteriostatic and fungistatic activity, Arzneimittel-Forschung (1964), vol. 14, No. 12, pp. 1301-1306.*

* cited by examiner

Mammalian Thioredoxin Reductase

*E. coli* Thioredoxin Reductase

BACTERIAL THIOREDOXIN REDUCTASE INHIBITORS AND METHODS FOR USE THEREOF

FIELD OF THE INVENTION

The present invention relates to the field of biologically active selenium and sulfur compounds, and more particularly to ebselen (or ebsulfur), its diselenide analog, and more generally to benzisoselenazole-3(2H)-one and derivatives thereof, salts thereof, pharmaceutical formulations thereof, and methods of use thereof.

BACKGROUND OF THE INVENTION

The thioredoxin (Trx), thioredoxin reductase (TrxR), and NADPH are together called the thioredoxin system, which serves as a hydrogen donor for ribonucleotide reductase and has a general powerful disulfide reductase activity (4, 5, 11, 13). The thioredoxin system is present in cells and in all forms of life (4, 5, 11, 13). Thioredoxin reductase (TrxR) is a dimeric FAD containing enzyme that catalyzes the reduction of its main protein substrate oxidized thioredoxin, to reduced thioredoxin at the expense of NADPH. The enzyme mechanism involves the transfer of reducing equivalents of NADPH to a redox active site disulfide via an FAD domain. Thioredoxin reductase from *Escherichia coli* with subunits of 35 kDa has been extensively characterized (46). X-ray crystal structure reveals that the active site disulfide is located in a buried position in the NADPH domain (22) and suggests that it should undergo a large conformational change to create a binding site for Trx-$S_2$ and reduction by a dithiol-disulfide exchange.

Thioredoxin reductase is a ubiquitous enzyme present in all cells. However, the enzyme is often over-expressed in tumor cells compared to normal tissues, and tumor proliferation seems to be crucially dependent on an active thioredoxin system, making it a potential target for anticancer drugs (16). Over the last decade a number small organic and organometallic molecules that include platinum and gold containing complexes (47-50) naphthoquinone spiroketal based natural products (51-53), different naphthazarin derivatives (54), certain nitrosoureas (55-56) and general thiol (or selenol) alkylating agents such as 4-vinylpyridine, iodoacetamide, or iodoacetic acid (57) have been identified as inhibitors of Trx or TrxR or both. Engman et al. have reported the inhibition of mammalian thioredoxin reductase by diaryldichalcogenides (58) and organotellurium compounds (59-61). However, no inhibition has been presented for bacterial TrxR.

Thioredoxins together with glutaredoxins are the two dithiol hydrogen donors for the essential enzyme ribonucleotide reductase required for DNA synthesis (FIG. 1) (4, 5). As shown in FIG. 1 the two enzymes glutathione reductase (GR encoded by the gor gene) and thioredoxin reductase (TrxR encoded by the trxB gene) in *E. coli* are central in electron transport from NADPH (6). Thioredoxin reductase from human and animal cells is a large selenoenzyme and very different from the enzymes present in all prokaryotes (7, 8). In contrast to the mammalian enzymes the *E. coli* enzyme is highly specific and utilizes a different mechanism with an involvement of protein conformation change as mentioned above (9).

Thioredoxin reductase (TrxR), catalyzes the electron donation from NADPH via thioredoxin (Trx) to ribonucleotide reductase (RNR) and may be essential for DNA synthesis if no other system is present. Cytosolic Trx is a highly conserved 12 kDa protein whereas the cytosolic TrxRs from mammalian and bacterial, e.g. *Escherichia coli*, are very different in their structure and catalytic mechanisms, with mammalian TrxR being a large selenoenzyme.

Ebselen, 2-phenyl-1,2-benzoisoselenazol-3(2H)-one is an antioxidant and anti-inflammatory selenoorganic compound (1) used in clinical trials against e.g. stroke (2). It is thus known to be safely administered to humans. Ebselen and ebselen diselenide have been reported as substrates for mammalian thioredoxin reductase (3a) and its reaction mechanisms have been published (3b, 32). There are several reports of synthesis of substituted benzisoselenazol-3(2H)-ones. Some of these compounds were reported as inhibitors of viral cytopathogenicity and active immunostimulants inducing cytokines, such as interferons (IFNs), tumor necrosis factors (TNFs) and interleukin (IL-2) in human peripheral blood leukocytes (62-64). However, none of the reports indicates thioredoxin reductase activity.

It has been shown that ebselen, which has been known as a glutathione peroxidase (GSPx) mimic (1), is a substrate for human and mammalian thioredoxin reductase and a highly efficient oxidant of reduced thioredoxin (3a,3b). This strongly suggested that the thioredoxin system (NADPH, thioredoxin reductase and thioredoxin) is the primary target of ebselen, since a highly efficient reduction of hydroperoxides was given by ebselen in the presence of the thioredoxin system (3).

SUMMARY OF THE INVENTION

Ebselen, a small isoselenazol drug well known for its antioxidant and anti-inflammatory properties, also has antibacterial properties. The mechanism has been unknown and there is a remarkable difference in sensitivity between *Staphyloccus aureus* being a 100-fold more sensitive than *E. coli* (10). The growth of methicillin resistant *Staphylococcus aureus* was shown to be inhibited by 0.20 μg per ml of ebselen, whereas strains of Enterobacteriaceae like *E. coli* NHHJ were much more resistant requiring up to 50 μg per ml. The MIC for 90% of *S. aureus* strains was 1.56 μg per ml and the drug was bacteriocidal (10).

Control of bacterial infection using chemotherapeutic principles and antibiotics are based on inhibition of cell wall synthesis, protein synthesis and other metabolic pathways. The presently used drugs have limitations and resistant bacterial infections is an increasing problem as evident by development of vancomycin and methicillin resistant bacteria. Since genetic material in the form of DNA is common to all microorganisms, inhibition of DNA synthesis is an attractive principle. In addition, drugs interrupting the defense of bacteria against oxidative stress should be a useful principle for developing new antibacterial agents.

The thioredoxin system, including thioredoxin (Trx), thioredoxin reductase (TrxR) and NADPH, is the most powerful protein disulfide reductase in cells (4, 5, 11-13). Together with the glutaredoxin system, including glutaredoxin (Grx), glutathione (GSH), glutathione reductase (GR) and NADPH, thioredoxins are important hydrogen donors of ribonucleotide reductase for DNA synthesis and play key roles in cell redox regulation and growth control (4-6, 12, 14).

Thioredoxin reductase is one of those few examples of enzymes where the same reaction is catalyzed by more than one structure and mechanism (9, 15). Extensive studies on the features and redox properties of TrxR from various organisms resulted in the classification of two TrxRs, one from higher eukaryotes with high molecular weight and structurally resembles the other oxidoreductases; the other from prokaryotes, fungi, and plants with low molecular weight and distinct in structures and catalytic mechanism. Thus the striking difference between the enzymes would make them ultimate targets for novel antibiotic drug designs (16) although this has not yet been reported.

The structural features of the mammalian TrxR and its *E. coli* counterpart are illustrated in FIGS. 2A and 2B. The TrxR from mammalian is a large selenoprotein with homodimer of 55 kD per subunits and a structure closely related to glutathione reductase but with an elongation containing a catalytically active selenol-thiol/selenosulfide in the conserved C-terminal sequence Gly-Cys(496)-Sec(497)-Gly, and thus a wide substrate specificity (7, 8, 15, 17-19). The bacterial counterpart of TrxR is however a non-selenoprotein with homodimer of 35 kD per subunits (9, 20, 21). As shown in FIG. 2B, each *E. coli* TrxR monomer consists of an NADPH-binding domain and an FAD binding domain connected by a double-stranded β-sheet. The active site Cys (135)-Ala-Thr-Cys(138) is located in the NADPH domain. A well-recognized characteristic of the *E. coli* enzyme is its large conformational change during catalysis. In its 3-D structure, the flow of electrons from NADPH to the active-site disulfide via the flavin can only be possible if the NADPH domain graphically rotating over 67° relative to the FAD domain, allowing an efficient hydride transfer from NADPH to FAD (the nicotinamide ring and the isoalloxazine would be in close contact) and simultaneously exposing the redox-active disulphide to the surface of the protein, accessible for the substrate (22, 23). Mammalian TrxRs, as shown in FIG. 2A, are large dimeric selenoproteins ($M_r$ 114.000), with structures closely related to glutathione reductase, but with a C-terminal 16 amino acid elongation containing a unique catalytically active conserved sequence Gly-Cys-Sec-Gly. Mammalian thioredoxin reductases have a remarkably wide substrate specificity. *E. coli* TrxR is smaller (Mr 70.000/dimer), with the active-site Cys-Ala-Thr-Cys disulfide loop located in the NADPH domain. During catalysis, a large conformational change is required, i.e., from FO (flavin oxidation by disulphide) to FR (flavin reduction by NADPH) form as discussed above.

Ribonucleotide reductase is a universal enzyme, which for aerobic organisms supply all four deoxyribonucleotides required for DNA synthesis de novo, for either replication or repair (FIG. 1). Electrons for the reduction ultimately are from NADPH via either thioredoxin or glutaredoxin. These two small protein thiol electron donors are reduced by separate pathways. Thioredoxin is reduced by thioredoxin reductase, and glutaredoxin by the tripeptide glutathione (GSH), which is present in high millimolar concentrations in most cells. Oxidized glutathione (GSSG) is reduced by glutathione reductase. The two systems do not cross-react.

Whereas, there are general overall similarities between thioredoxin, glutaredoxin and ribonucleotide reductase in bacteria and human and other mammalian cells, there are fundamental differences between thioredoxin reductase enzymes. Thus, the enzyme is by convergent evolution either low molecular weight specific enzymes like that in *E. coli* or other bacteria or a high molecular weight selenocysteine-containing enzyme with broad specificity like the three isozymes in human cells.

Ebselen, 2-phenyl-1,2-benzoisoselenazol-3(2H)-one, is an isoselenazol well known for its antioxidant and anti-inflammatory properties (1, 24) and is widely used in laboratories as peroxide reducing antioxidant in in vivo models and has been proved in clinical trails against acute ischemic stroke (2, 25-31). We have previously shown that ebselen and its diselenide are substrates for mammalian TrxR and efficient oxidants of reduced Trx forming the ebselen selenol, the active form of ebselen with its hydrogen peroxide reductase activity (3a,3b). The mechanism of antioxidant action of ebselen, together with its diselenide, was mainly through its interactions with the mammalian TrxR and Trx, providing the electrons for the reduction of hydrogen peroxide from NADPH (3a, 3b, 32) (FIG. 3). In the present invention we have discovered that ebselen, however, is not a substrate of *E. coli* TxrR, but instead it is a competitive inhibitor for the reduction of thioredoxin with a $K_i$ of 0.15 μM. *E. coli* mutants lacking a functional glutaredoxin system (glutathione reductase, GSH or glutaredoxin 1) were much more sensitive to inhibition by ebselen, which thereby will inhibit the essential enzyme ribonucleotide reductase (RNR) required for DNA synthesis. A main target of action of ebselen is the thioredoxin system. It follows that gram positive bacteria or other microorganisms lacking GSH will be particularly susceptible to ebselen. The present invention demonstrates that the well tolerated drug ebselen inhibits bacterial growth due to the large differences in structure and mechanism of the bacterial and mammalian thioredoxin reductases, establishing the drug as a novel chemotherapeutic principle.

It has been reported that ebselen inhibits bacteria growth with much higher sensitivity towards *Staphylococcus aureus* than *E. coli* (10, 33). However the mechanism behind this inhibition was not previously known. The present inventors have found that ebselen and its diselenide are strong inhibitors of *E. coli* TrxR. In bacterial inhibition experiments using mutant strains lacking the enzyme glutathione reductase (GR encoded by the gor gene) or glutathione (gshA⁻ strain can not synthesize GSH) showed increased sensitivity towards ebselen. The interaction mechanism of ebselen and its diselenide with *E. coli* was studied showing the formation of a relative stable ebselen-TrxR complex at the active site of the enzyme. Interestingly, we found that the sulfur analogue of ebselen, ebsulfur (PZ25), and its disulfide were not inhibitors of the *E. coli* enzyme, but rather were substrates for the *E. coli* TrxR (FIG. 3). However, as shown below, this is not the case for all bacterial enzymes since the *Helicobacter pylori* TrxR is inhibited.

Comparing the kinetic parameters of the interaction between the compounds and the two enzyme systems, provides better understanding of the chemical basis for the inhibition mechanism of ebselen and its diselenide towards the *E. coli* TrxR. This enhanced understanding of the principle chemical mechanism of ebselen diverse activity towards mammalian and *E. coli* TrxR is very important for the use of the drug and also for the development of effective antibiotic drugs based on same mechanism.

Furthermore, the finding that ebselen can inhibit *E. coli* TrxR leads us to a search for the new organoselenium compounds containing the basic structure of ebselen, to study their reactivity with *E. coli* thioredoxin reductase. We synthesized benzisoselenazol-3(2H)-ones and studied their reaction towards the thioredoxin reductase, to find out the relationship between the structure and reactivity. These compositions have, to varying extent, inhibitory effects on *E. coli* TrxR and bacterial growth, and therefore may be useful as antibiotics.

Different classes of benzisoselenazol-3(2H)-one compounds such as N-aryl (EbSe 7-10), N-unsubstituted (EbSe 6), N-alkyl (EbSe 2-4), N-2-pyridyl (EbSe 11 & 12) and N-4-pyridyl (EbSe 13) substituted benzisoselenazol-3(2H)-ones as well as bis-benzisoselenazol-3(2H)-ones (EbSe 14-16) were synthesized. Their inhibition effect on *E. coli* thioredoxin reductase (TrxR) was studied by thioredoxin dependent DTNB disulfide reduction assay in vitro. Detailed kinetic studies show that bisbenzisoselenazol-3(2H)-ones compounds (EbSe 14-16) inhibit TrxR at nanomolar concentrations while compounds EbSe 7-10, 12-13, 2-4 and parent ebselen, 2-phenyl-1,2-benzisoselenazol-3(2H)-one (EbSe 6) inhibit at micromolar concentrations. Other compounds did not inhibit *E. coli* TrxR. Tryptophan fluorescence measurements were carried out to follow the reaction of these compounds with reduced thioredoxin Like ebselen, these compounds also rapidly oxidized reduced thioredoxin.

BRIEF DESCRIPTION OF THE DRAWINGS

In FIG. 6A, 10 μM of ebselen (▲) and 10 μM of PZ25 (■) were used as substrate of 25 nM calf thymus TrxR. In FIG. 6B, 10 μM of PZ25 was used as substrate for 10 nM calf thymus TrxR (○) and 10 nM of *E. coli* TrxR (●). Reactions were started by adding enzymes in cuvettes containing 500 μl TE buffer with 100 μM NADPH, of which the consumption were followed by the changes of the absorption at 340 nm against identical blank without enzymes.

FIG. 10 shows the effect of Ebselen in the growth of wild type (○), trxA⁻C⁻ (*), gshA⁻ (●) and gshA⁻trxA⁻ (♦) strains in LB medium. Growth (A600) was determined 9 hrs after inoculation.

DETAILED DESCRIPTION OF THE PREFERRED EMBODIMENTS

Experiments

Materials and Enzymes

Figure 1:
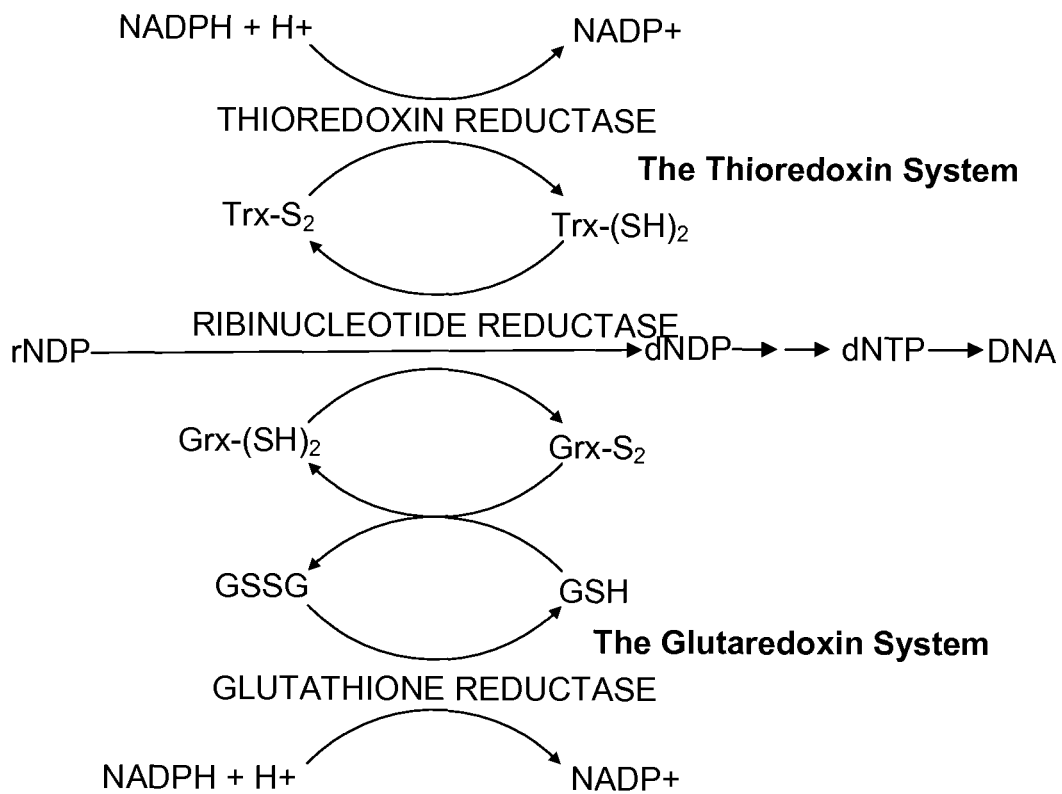
FIG. 1 schematically shows the thioredoxin and glutaredoxin biochemical systems, in which ribonucleotide reductase is essential for the synthesis of deoxyribonucleotides for DNA replication and repair and thioredoxin system and the glutaredoxin system supply electrons from NADPH.
Figure 2A:
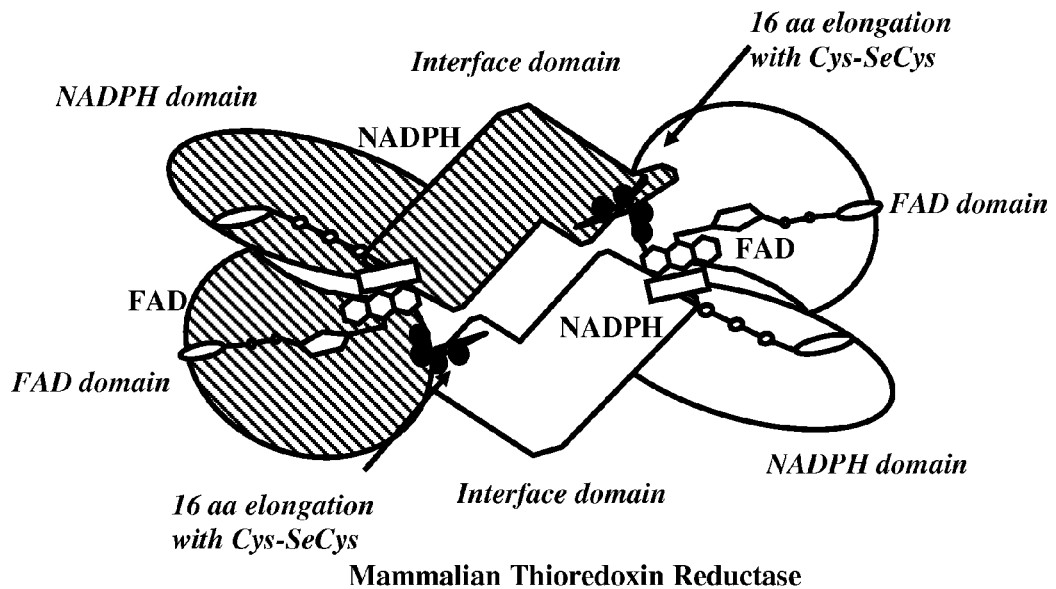
FIGS. 2A and 2B shows the conformational difference of mammalian and *E. coli* thioredoxin reductase.
Figure 2B:
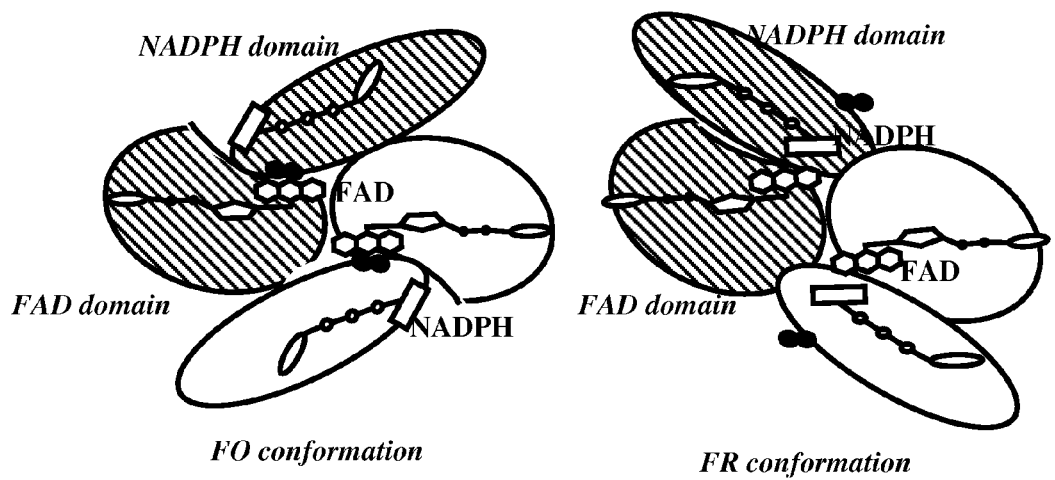

NADPH, DTT, DTNB, DMSO, insulin, and bovine serum albumin (BSA) were acquired from Sigma-Aldrich. Calf thymus TrxR and *E. coli* TrxR and Trx were acquired from IMCO corporation Ltd, Stockholm, Sweden (www.imcocorp.se). Rat glutathione reductase was a pure preparation prepared according to the method previously published (4). *H. pylori* TrxR and Trx were prepared as described before (66). Ebselen, $^{14}$C-labelled ebselen, ebselen diselenide and PZ25 (ebsulfur) were products of Daiichi, Tokyo, Japan and were dissolved in fresh DMSO before addition into the solution. Concentrations of DMSO were less than 5% of the solvent buffer, effective in dissolving the drugs. *E. coli* DHB4 strain wt, gor⁻, gshA⁻ were described as the reference (Prinz, W. A., Aslund, F., Holmgren, A. & Beckwith, J. (1997) J Biol Chem 272, 15661-7.)

Compounds Synthesis

All reactions were performed under inert atmosphere using Schlenk techniques. All solvents were purified by the standard procedures [65] and were freshly distilled prior to use. All chemicals were purchased from Sigma-Aldrich or Lancaster and used as received. $^1$H NMR spectra were recorded in CDCl₃ or DMSO-d₆ on a Varian VXR spectrometer operating at 400 MHz and chemical shifts are reported in ppm relative to TMS. Benzisoselenazol-3(2H)-one (EbSe 2-13) and bisbenzisoselenazol-3(2H)-one (EbSe 14-16) were prepared from 2-(chloroseleno)benzoyl chloride using the synthetic procedure described in the literature with slight modifications [62-64].

Enzyme Assays

The activity of the enzyme was determined at room temperature using an Ultrospec 3000 UV/Visual spectrophotometer (Amersham Biosciences). Measurements of TrxR activity from both calf thymus and *E. coli* were performed in a buffer containing 50 mM Tris-Cl, 1 mM EDTA, pH 7.5, generally with 100 μM NADPH and the indicated amount of the drugs. The enzyme-catalysed reactions were followed at 340 nm using the standard calculation of NADPH oxidation to NADP$^+$ with a molar extinction coefficient of 6200 M$^{-1}$ cm$^{-1}$ (32, 34). The conditions of the assay of bacterial thioredoxin reductase have been described (32, 34) using either 1 mM DTNB or 160 µM insulin as a substrate. In DTNB coupled assays, 240 µM NADPH and 1 mM DTNB were used in the TE buffer and formation of the TNB was measured at 412 nm, where TNB has an extinction coefficient of 13600 M$^{-1}$ cm$^{-1}$.

The spectrum of PZ25 (ebsulfur) and its disulphide showed similar patterns as that of their selenium analogues (3, 32). PZ25 has somewhat weaker absorption band in the region 250 to 530 nm, with a $\epsilon_{340}$ of 3720 M$^{-1}$ cm$^{-1}$ (5000 M$^{-1}$ cm$^{-1}$ for ebselen). PZ25 disulphide has absorption band at 250 nm to 450 nm region with $\epsilon_{340}$ of (EbS)$_2$ of ca 16000 M$^{-1}$ cm$^{-1}$, while the $\epsilon_{340}$ of the selenium analogue is ca 21000 M$^{-1}$ cm$^{-1}$.

E. coli Strains and Growth Conditions

E. coli strains wild type, gor$^-$ lacking glutathione reductase, and grxA$^-$ lacking synthesis of glutathione were used in this work (Table 1). Strain trxA$^-$C$^-$ was a kind gift of Eric J. Stewart, Department of Microbiology and Molecular Genetics, Harvard Medical School.

Bacterial cells were grown in 5 mL cultures at 37° C., 120 rpm in 15 mL closed tubes containing Lutria-Bertani (LB) or M9 minimal media supplemented with 50 µg/ml Leu, Ile, 1× basal medium Eagle's vitamin solution (Invitrogen) and 2 µg/mL nicotinic acid. For the experiments regarding sensitivity of growth to ebselen, cells were initially grown overnight at 37° C. at the respective medium. The next day, equal cell numbers (as determined by A$_{600}$) with dilutions of at least 1:50 were used to start 5 mL cultures containing different concentrations of Ebselen. Ebselen stock solutions were freshly prepared in DMSO. Extra DMSO was added to the cultures so that the total volumes of DMSO were the same per culture even at different final concentrations of Ebselen. Growth inhibition assays were carried out also on M9 minimal plates. The plates were covered with minimal top agar that contained equal cell number for all the strains examined. These were derived from overnight liquid cultures in M9 medium.

Sensitivity to ebselen was measured by inhibition of growth as determined by scattering (absorbance) at 600 nm at different times after inoculation.

TABLE 1

E. coli DHB4 Strains

| Strain | Genotype | source |
|---|---|---|
| Wt | wild type DHB4 | (35) |
| trxB$^-$ | trxB::Kan | (35) |
| gor$^-$ | gor522 . . . mini-Tn10Tc | (35) |
| gshA$^-$ | gshA20::Km | (35) |
| gshA$^-$trxA$^-$ | gshA20::Km, ΔtrxA | (35) |
| trxA$^-$C$^-$ | ΔtrxA, ΔtrxC, nadB::Tn10Tc | Eric J. Stewart |

Inhibition of Mycobacterium tuberculosis by Ebselen

The test was done in the radiometric BACTEC 460 system as described by Hoffner et al. J. Antimicrobial Chemotherapy (1997) 40, 885-888, recording the metabolic activity of the mycobacterium as radioactive $^{14}$C-labelled carbon dioxide produced during a 8-10 day period with daily recordings (GI index).

Inhibition of Helicobacter pylori

The bacteria were cultured in 96-well microtiter plates with a microaerophilic environment at 37° C. for 4 days. The whole amount of the wells was then plated on GC agar plates containing different concentrations of ebselen. Ebselen was diluted in a two-fold series (0.39-200 µg/ml), the minimal bactericidal concentration (MBC) was determined by the first concentration with a total bactericidal effect.

Measurement of IC50 of Ebselen Derivates for E. coli TrxR

For screening of different classes of ebselen derivatives as inhibitors of E. coli TrxR, the compounds of different concentration (1-40 µM) were incubated for a minute with mixture containing 100 nM E. coli TrxR, 200 µM NADPH and 2 µM of E. coli Trx. Then 1 mM DTNB was added and the enzyme activity was followed by the initial linear increase at A412 for 5 minutes.

Measurement of K$_i$ of Ebselen Derivates for E. coli TrxR

The detailed inhibition studies using 0.001-4 µM inhibitor were performed in quartz cuvettes and the assay mixture of 500 µL containing E. coli TrxR (6 nM), E. coli Trx (1 or 2 or 4 µM), NADPH (240 µM), and DTNB (1 mM using Zeiss or Ultrospec 3000 Uv-visible spectrophotometer. E. coli TrxR activities were subsequently determined using the standard DTNB assay.

Detection of Reversibility of E. coli TrxR Inhibition by Ebselen Derivates

For the reversible inhibition, 600 nM TrxR was incubated with 400 µM NADPH in the absence (control) or presence of 320 µM inhibitor for 30 minutes in total volume of 500 µL of 50 mM Tris-cl pH 7.5, 2 mM EDTA pH 8.0 (TE buffer) TE buffer for 30 minutes. The samples were desalted by gel chromatography on a NAP-5/NAP-10 columns (Amersham bioscience) using N$_2$-equilibrated TE buffer. Enzyme activities of desalted proteins were performed using Ultrospec 3000 UV-visible spectrophotometer. Also second set of incubated samples were centrifuged using filter membrane tubes and the activity of proteins were measured.

Fluorescence Experiment

For the preparation of Trx-(SH)$_2$, the E. coli Trx-S$_2$ was incubated with 1 M DTT for 20 minutes and DTT was subsequently removed by gel chromatography on an NAP-5 column (Amersham bioscience) by using N$_2$-equilibrated TE buffer. Trx-(SH)$_2$ was mixed with benzisoselenazol-3(2H)-one derivatives in a total volume of 3 ml TE buffer containing 50 mM Tris-cl/2 mM EDTA, pH 7.5. Excitation of fluorescence at 295 nm and emission spectra in the range of 310-460 nm were recorded. Emission at 345 nm was followed to record the rate of oxidation of Trx-(SH)$_2$ by benzisoselenazol-3(2H)-one derivatives. Reduced TrxR was obtained by the incubation of oxidized TrxR with NADPH and similar experiment repeated to see the effect benzisoselenazol-3(2H)-one derivatives. Excitation of fluorescence at 380 nm and emission at 510 nm was followed.

Bacterial Inhibition by Ebselen Derivates

E. coli DHB4 strains wt, gshA$^-$, gor$^-$, oxyR$^-$ were cultured overnight in LB medium. Then the cultures were diluted 100 times and incubated in 96 well plates with different concentration of ebselen derivates (6.25, 12.5, 25, 50 & 100 µM) at 37° C. for 4 hrs. OD 600 was detected and DMSO was used as the control. Minimum Inhibition concentration (MIC) was defined the ebselen derivates concentration in which OD600 was below 10% of the culture treated by DMSO. The data are the means of two experiments.

Inhibition of H. pylori TrxR by Ebsulfur (PZ-25).

100 nM H. pylori TrxR was incubated with 0, 4, 20, 40 µM of ebsulfur in 0.50 ml semi-microcuvettes containing 0.20 mM NADPH, in 0.10 M Tris-Cl, pH 8.0, 1 mM EDTA for 10 min, then 4 µM of H. pylori Trx and 160 µM insulin was added in the solution to initiate the reaction, *H. pylori* TrxR activity was represented by NADPH consumption.

Inhibition of the Growth of *H. pylori* by PZ-25 (Ebsulfur).

Clinically isolated and standard *H. pylori* strains were cultured for 4 days in F12 medium with 5% FBS. PZ-25 was diluted in a two-fold series, the minimal bactericidal concentration (MBC) was determined by the first concentration with a total bactericidal effect. Ebselen and methronidazole were used as the control.

Results

Ebselen and Ebselen Diselenide are Strong Competitive Inhibitors Towards *E. coli* TrxR.

Figure 4A:
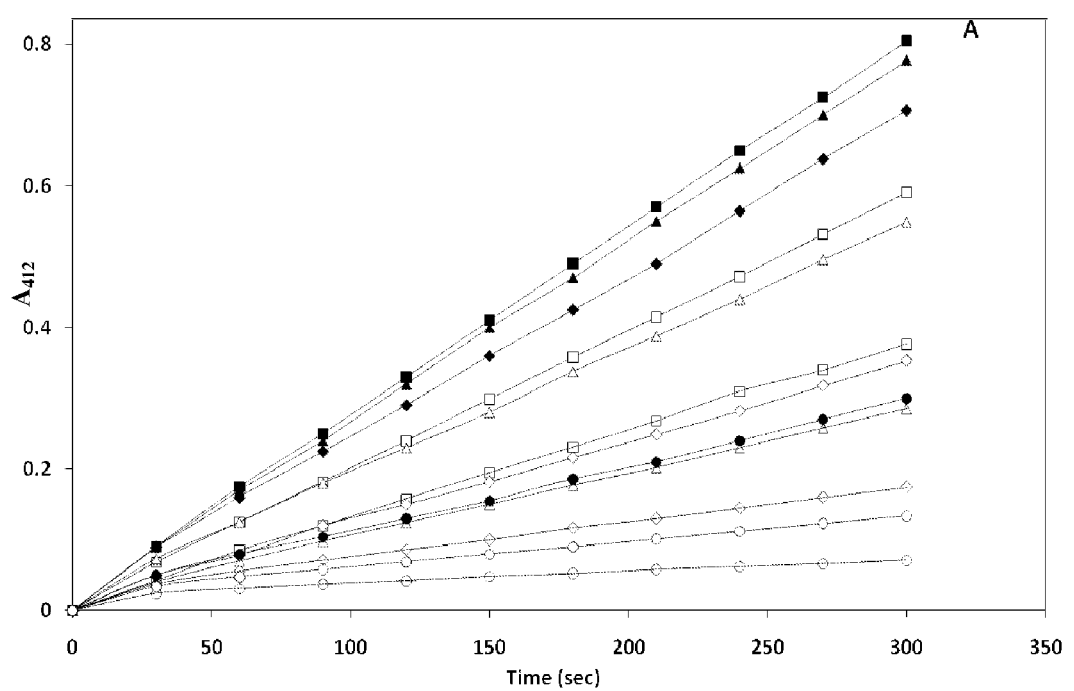
FIGS. 4A and 4B show the effect of ebselen (FIG. 4A) and ebselen diselenide (FIG. 4B) on DTNB reduction by *E. coli* thioredoxin and thioredoxin reductase. Assays were contained in 0.50 ml semi-microcuvettes containing 0.24 mM NADPH, 1 mM DTNB in 0.10 M Tris-Cl, pH 8.0, 1 mM EDTA. The increase in $A_{412}$ was measured against a blank using 10 nM *E. coli* TrxR in the presence of 2 μM (grey filled points), 5 μM (white filled points), 10 μM (black filled points) *E. coli* Trx with 0 (squares), 0.5 μM (triangles), 1 μM (rhombus), 2 μM (rounds) of ebselen or ebselen diselenide.
Figure 4B:
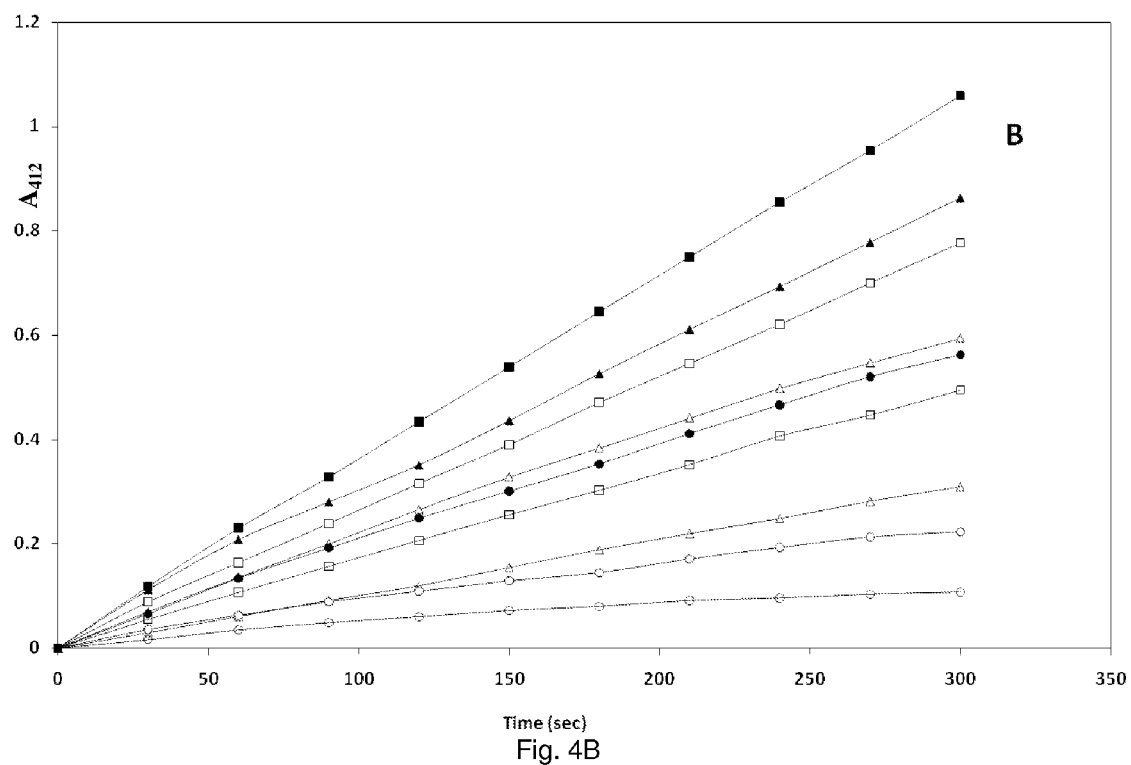

When ebselen and ebselen diselenide are directly added in the solutions of *E. coli* TrxR and NADPH, no oxidations of NADPH were found. This is in line with the known fact that *E. coli* TrxR is strictly specific towards *E. coli* Trx. Further we examined the effect of ebselen in the reduction of disulphide by *E. coli* Trx and TrxR using both DTNB and insulin as substrates. As shown in FIGS. 4A and 4B, ebselen and its diselenide strongly inhibited the *E. coli* TrxR reduction towards *E. coli* Trx in a typical DTNB coupled assay. The same inhibition patterns are also shown for ebselen and ebselen diselenide in the insulin reduction assays (data not shown). FIGS. 4A and 4B show the effect of ebselen (4A) and ebselen diselenide (4B) on DTNB reduction by *E. coli* thioredoxin and thioredoxin reductase. Assays in semi-microcuvettes with 0.5 ml solution contained 0.24 mM NADPH, 1 mM DTNB in 50 mM Tris-Cl/1 mM EDTA, pH 7.5 buffer. (A) In the presence of 2 µM (grey filled points), 5 µM (white filled points) and 10 µM (black filled points) of *E. coli* Trx and 7.6 nM of *E. coli* TrxR with ebselen at concentrations of zero (squares), 0.5 µM (triangles), 1 µM (rhombus), and 2 µM (rounds), the increase in $A_{412}$ was measured against a blank. (B) In the presence of 2 µM (grey filled points), 5 µM (white filled points) and 10 µM (black filled points) of *E. coli* Trx and 10 nM of *E. coli* TrxR, with ebselen diselenide at concentrations of zero (squares), 1 µM (triangles) and 2 µM (rounds), the increase in $A_{412}$ was measured against a blank.

*E. coli* Trx largely increases the rate of reduction of ebselen and ebselen diselenide by mammalian TrxR (3, 32). Direct reduction of ebselen and the diselenide reduced *E. coli* Trx also were observed by fluorescence spectroscopy and the second-order rate constants were determined to be $2 \times 10^7$ $M^{-1}s^{-1}$ and $1.7 \times 10^3$ $M^{-1}s^{-1}$, respectively (32). Thus ebselen and the diselenide are targeting the *E. coli* TrxR rather than the *E. coli* Trx.

Figure 5A:
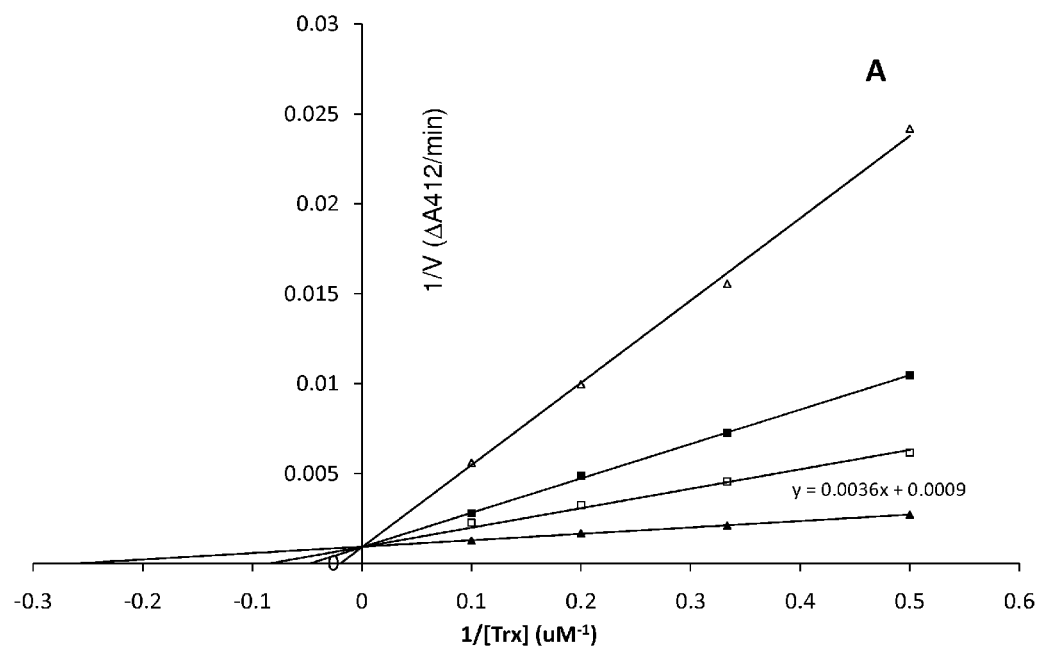
FIGS. 5A and 5B show Lineweaver-Burk plots for the inhibition of ebselen (FIG. 5A) and ebselen diselenide (FIG. 5B) on the activity of *E. coli* TrxR with Trx as measured by DTNB coupled assay. (A) Ebselen concentrations were 0 μM (▲), 0.5 μM (∀), 1 μM (■) and 2 μM (Δ). The $K_i$ derived from these slopes is 0.14±0.05 μM. (B) Ebselen concentrations were 0 μM (▲), 1 μM (■) and 2 μM (∀). The K, derived from these slopes is 0.46±0.05 μM.
Figure 5B:
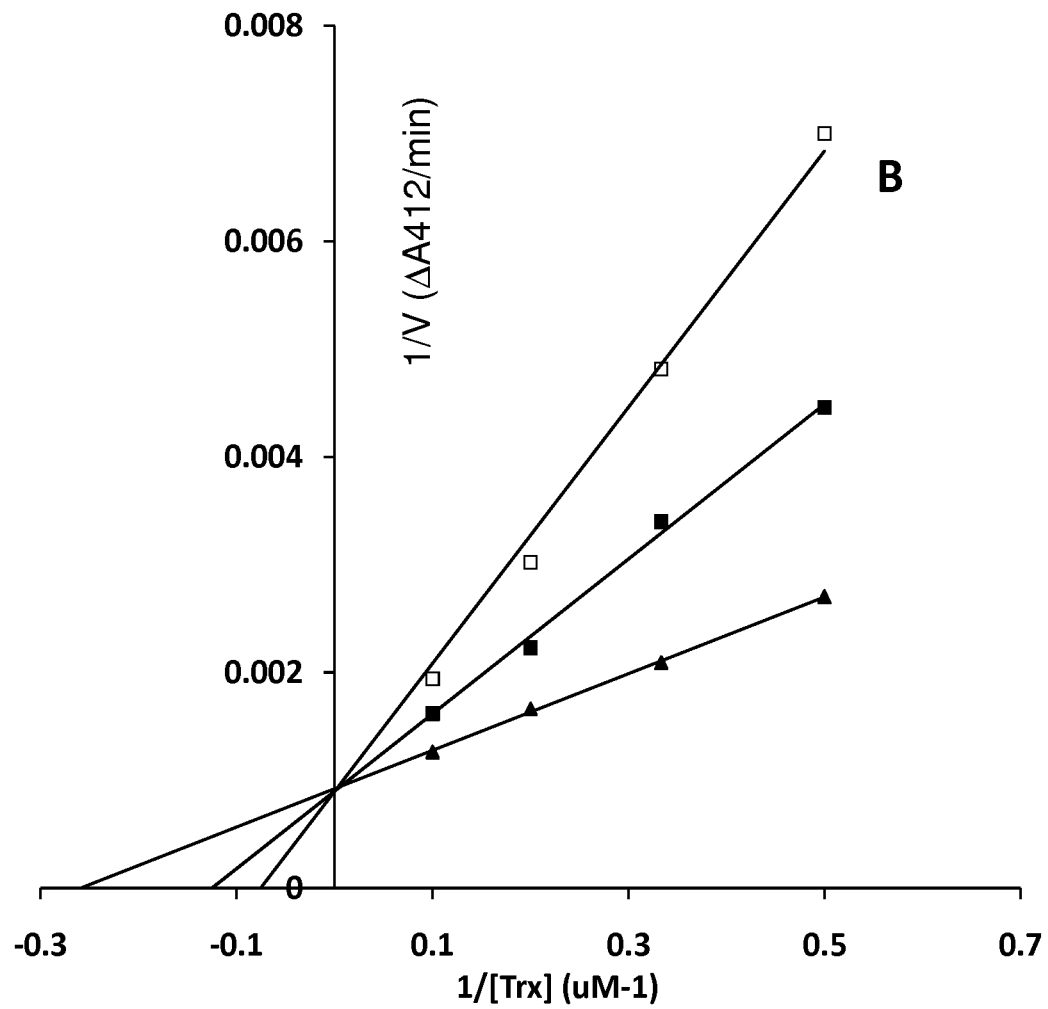
Figure 6A:
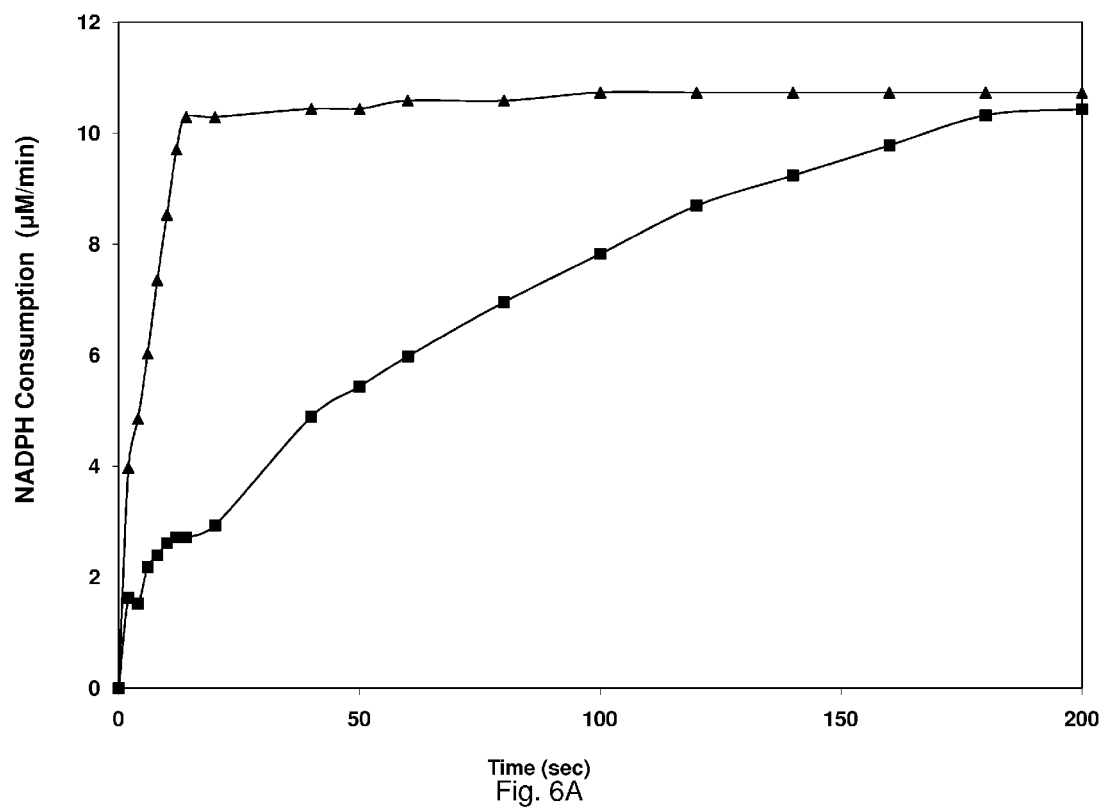
FIGS. 6A and 6B show ebselen and its sulphur analogue, PZ25, as substrates of calf-thymus TrxR and PZ25 as substrate of *E. coli* TrxR.
Figure 6B:
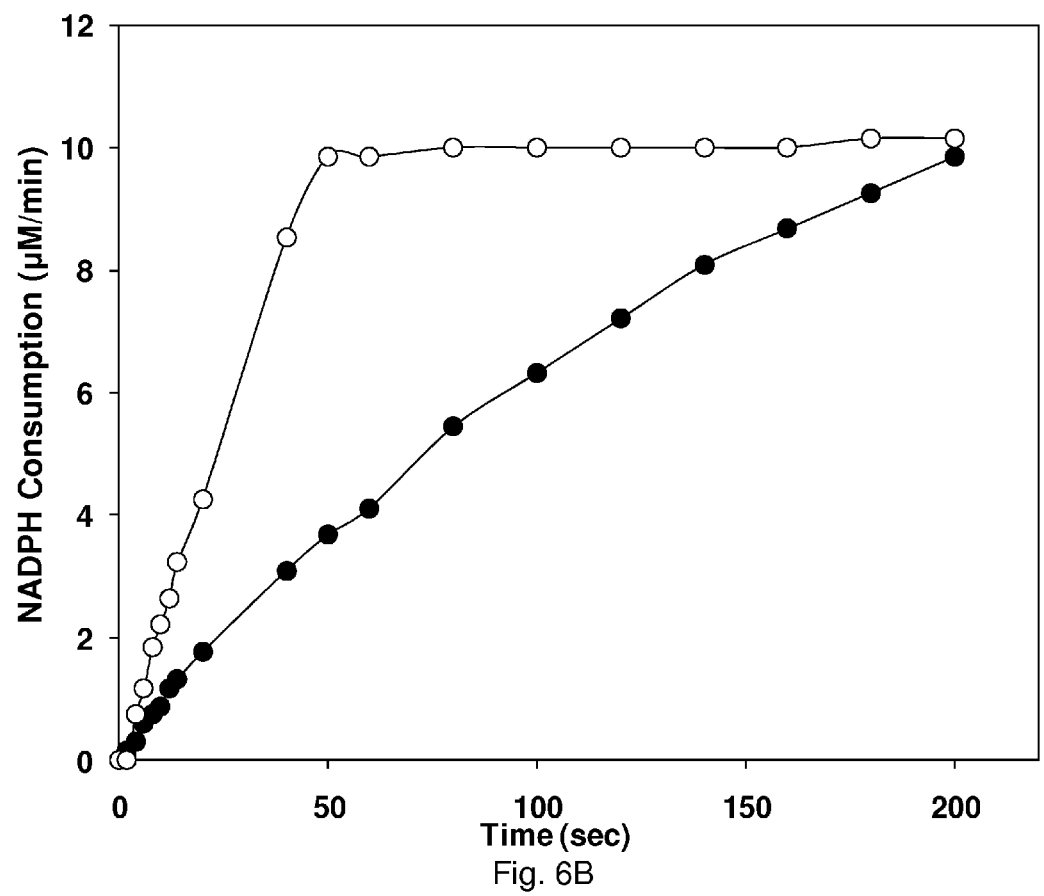
Figure 7:
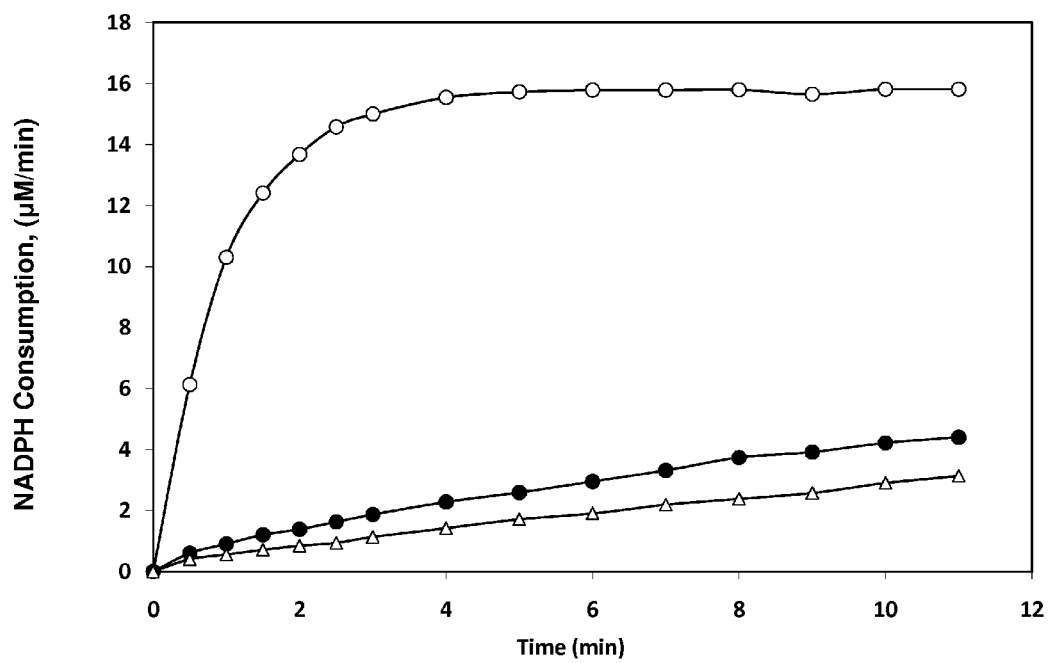
FIG. 7 shows ebselen diselenide and its sulphur analogue, PZ25 disulphide, as substrates of calf-thymus TrxR and PZ 25 disulphide as substrate of *E. coli* TrxR. Ebselen diselenide (Δ) and PZ25 disulfide (○) were reduced with 10 nM calf thymus TrxR, while PZ25 disulphide was reduced by 10 nM of *E. coli* TrxR (●). Reactions were started by adding enzymes to cuvettes containing 500 μl TE buffer with 100 μM NADPH and 16 μM compounds. The NADPH consumption was followed by the changes of the absorption at 340 nm against identical blank without enzymes.

From FIGS. 4A and 4B, we see that the degree of inhibition caused by ebselen depends on the concentrations of Trx and ebselen. An increase in [Trx] at constant [EbSe] decreases the degree of inhibition and an increase in [EbSe] at constant [Trx] increases the degree of inhibition, showing a typical competitive inhibition towards the TrxR. A series of Lineweaver-Burk plots of the initial rate for the reduction of DTNB in the presence of ebselen and ebselen diselenide gave a typical pattern of competitive inhibitions are shown in FIGS. 5A and 5B. The dissociation constants $K_i$ for the ebselen-TrxR and ebselen diselenide-TrxR complexes derived from the slopes [$(K_M/k_{cat})(1+[I]/K_i)$] were 0.14±0.05 µM and 0.46±0.05 µM, respectively.

TABLE 2

Kinetic parameters determined for ebselen, its diselenide and their sulphur analogues with mammalian and *E. coli* TrxR.

| Compounds | Mammalian TrxR | | | *E. coli* TrxR | | |
|---|---|---|---|---|---|---|
| | $k_{cat}$ (min$^{-1}$) | $k_M$ (µM) | $k_{cat}/K_M$ (µM$^{-1}$min$^{-1}$) | $k_{cat}$ (min$^{-1}$) | $k_M$ (µM) | $k_{cat}/K_M$ (µM$^{-1}$min$^{-1}$) |
| EbSe[a] | 588 | 2.5 | 235 | Inhibitor with $K_i$ = 0.15 ± 0.05 µM | | |
| (EbSe)$_2$[b] | 79 | 40 | 2 | Inhibitor with $K_i$ = 0.46 ± 0.03 µM | | |
| EbS | 1400 | 2.5 | 560 | 700 | 2.5 | 280 |
| (EbS)$_2$ | 1500 | 47 | 32 | 100 | 27.6 | 3.63 |

[a]from ref (3);
[b]from ref (32).

Ebselen Inhibits the Growth of *E. coli* Strains and More Sensitive Towards gor$^-$ and grxA$^-$ Mutants.

Figure 3:
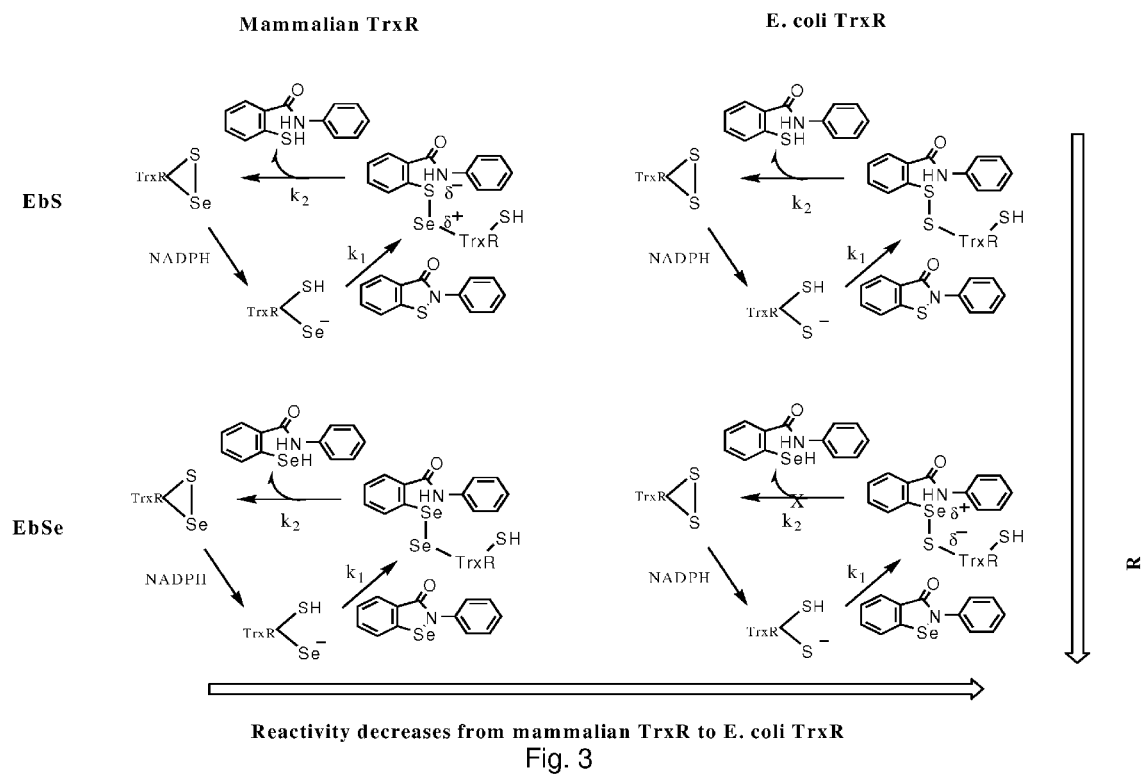
FIG. 3 shows the interaction of ebselen (EbSe) and ebsulfur (EbS) with mammalian and *E. coli* thioredoxin reductase.
Figure 8:
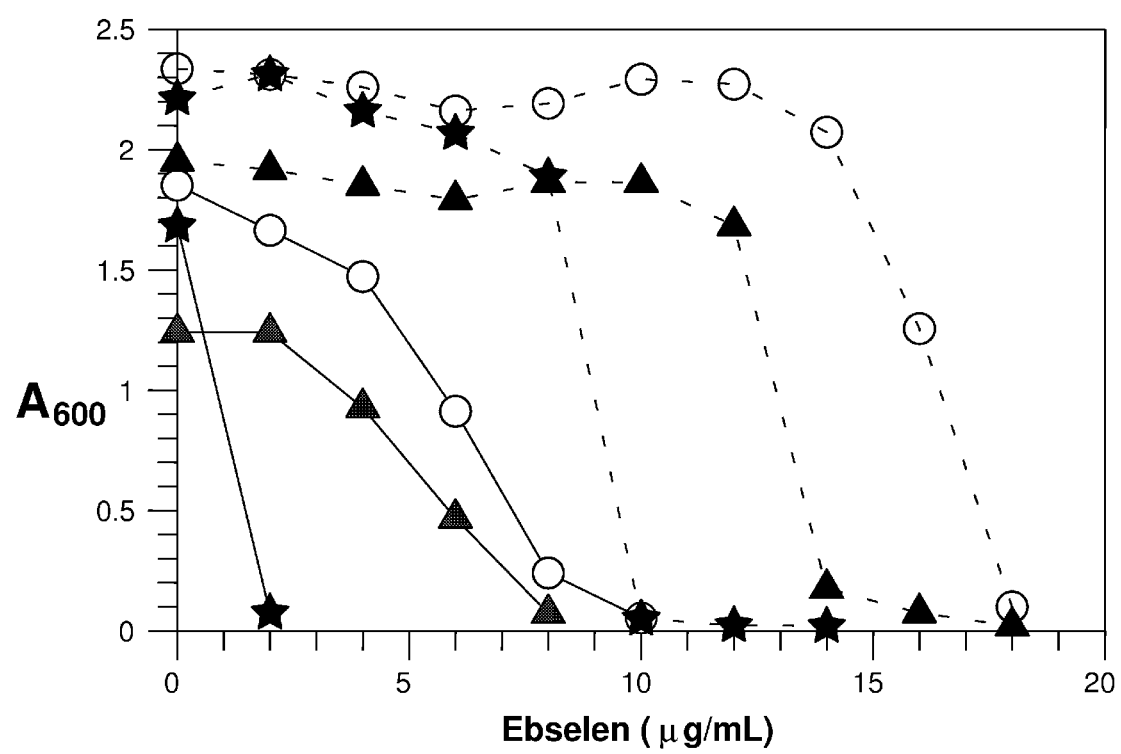
FIG. 8 shows the effect of ebselen in the growth of wild type (○), gor⁻ (★) and trxB⁻ (▲) strains in LB medium. Growth (A600) was measured 7 (solid lines) or 22 (dotted lines) hrs after inoculation.
Figure 9:
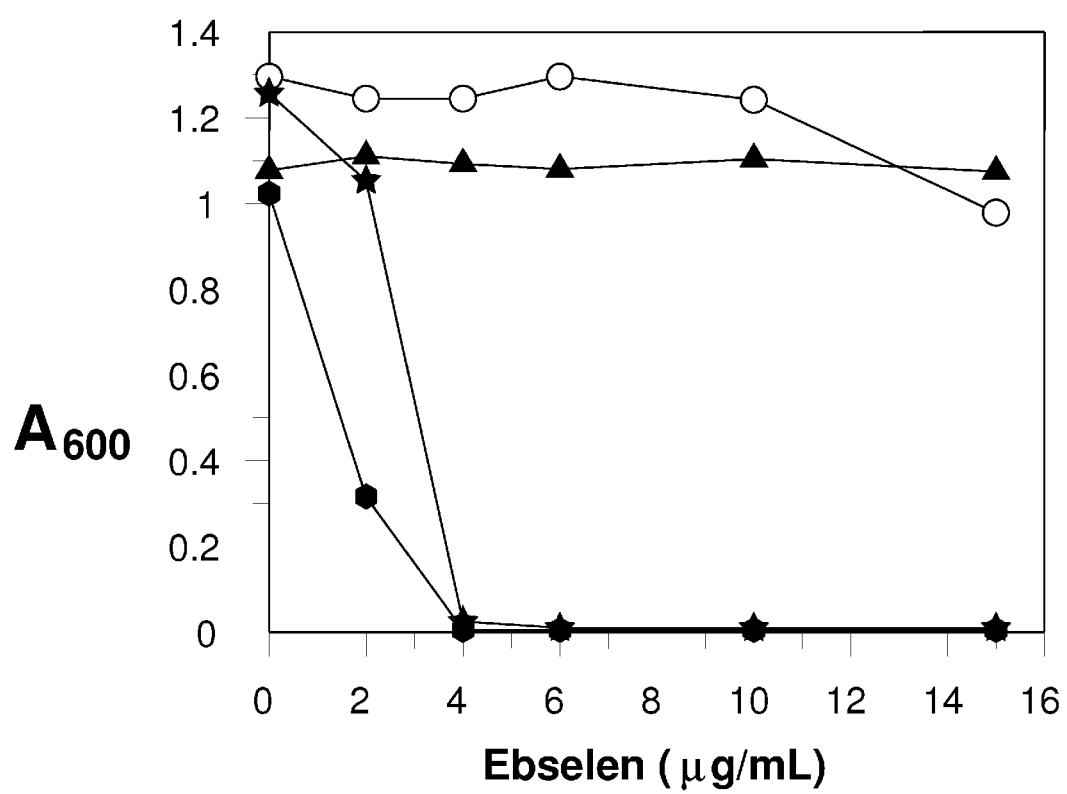
FIG. 9 shows the effect of Ebselen in the growth of wild type (○), trxB⁻ (▲), gor⁻ (★), and gshA⁻ (●) strains in M9 medium. Growth (A600) was measured 21 hrs after the onset of inoculation.
Figure 10:
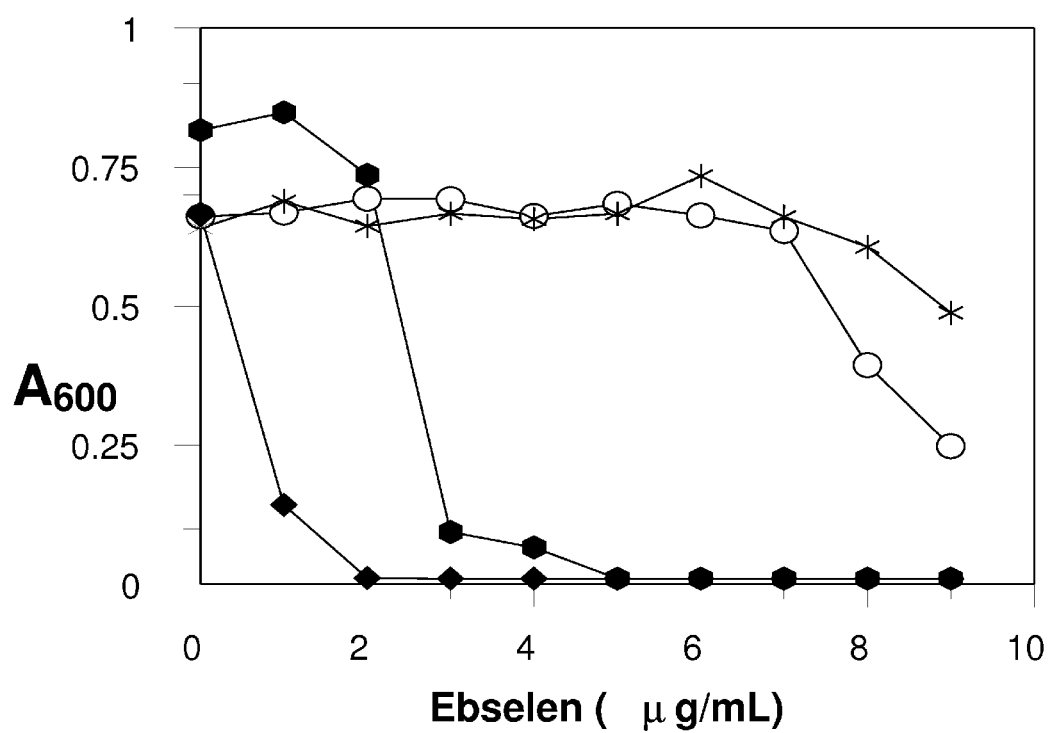
Figure 11:
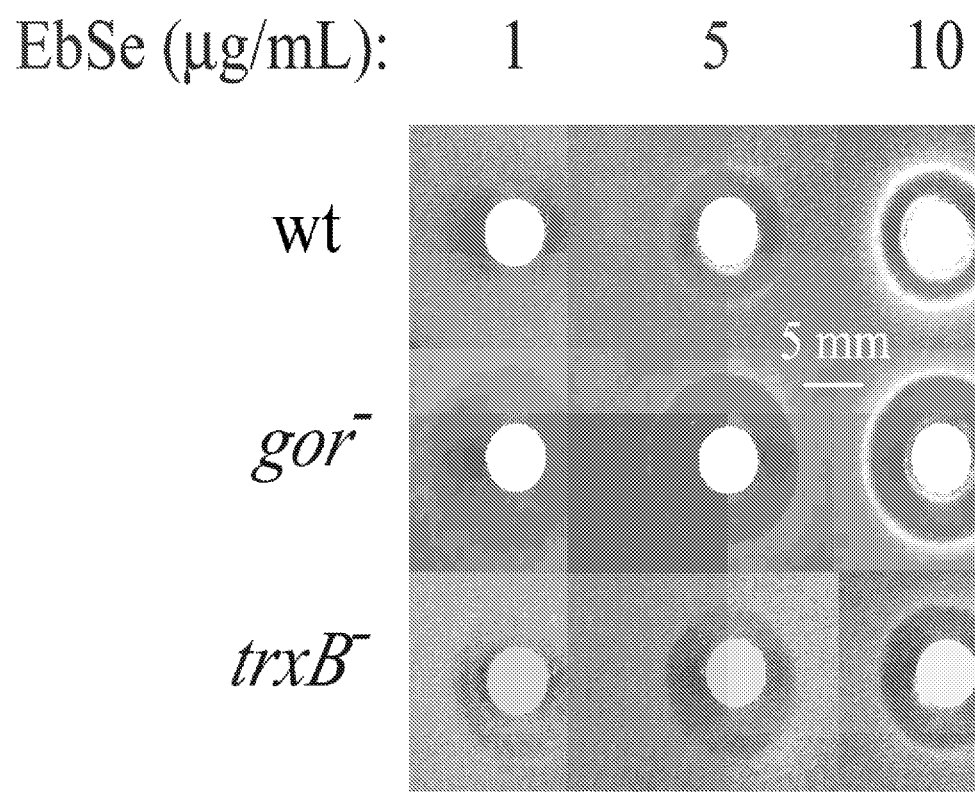
FIG. 11 shows a comparison of inhibition zones of ebselen in wild type, gor⁻ and trxB⁻ strains after 18 hrs of growth.
Figure 12A:
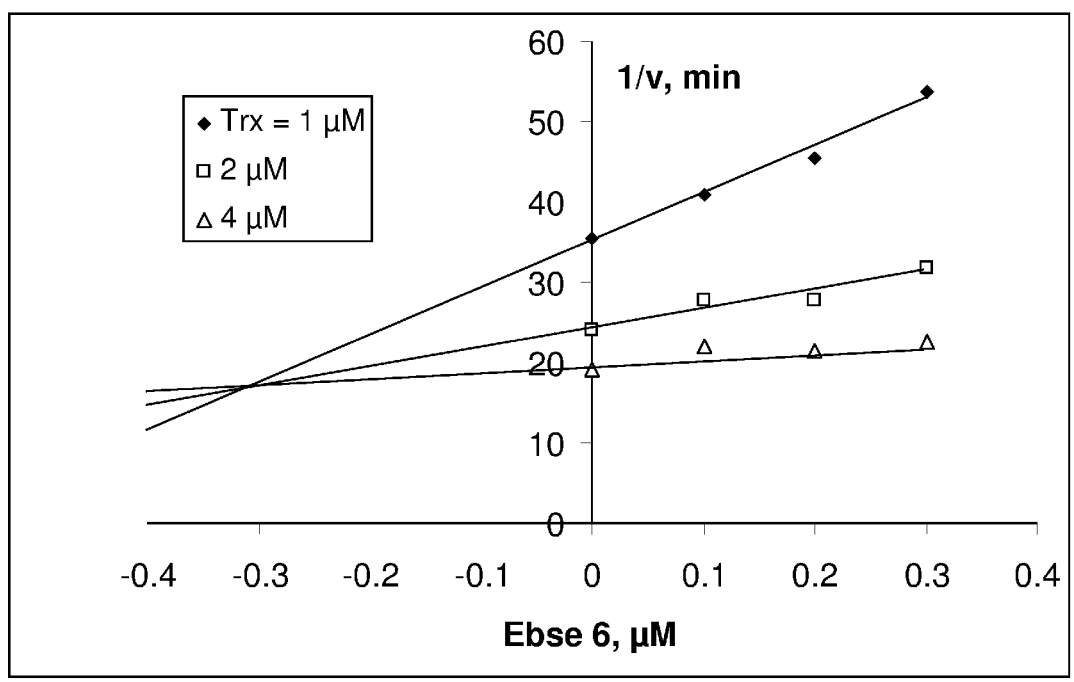
FIGS. 12A-12F show the $K_i$ value of ebselen derivates on *E. coli* TrxR, wherein different concentrations of ebselen derivates were incubated in 0.5 ml of 50 mM Tris-Cl, 2 mM EDTA, pH 7.5 containing 240 mM NADPH with 6 nM *E. coli* TrxR and *E. coli* TrxR (1, 2 or 4 μM), and then 1 mM DTNB was added, and the reaction was followed at A412 against control with same amount of enzyme and DMSO.
Figure 12B:
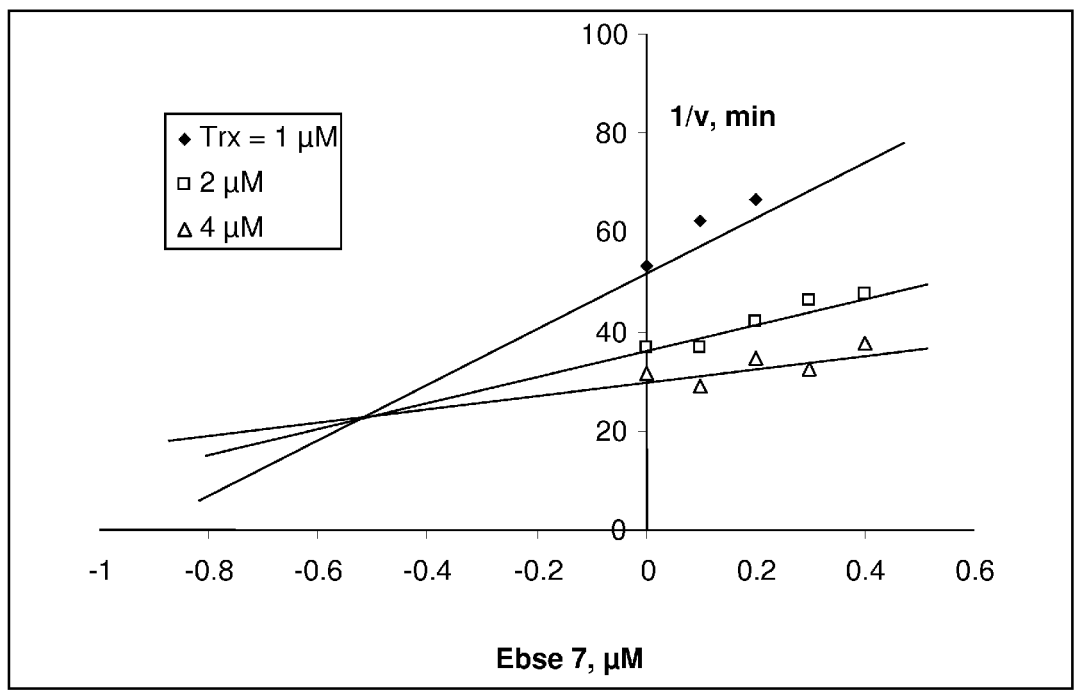
Figure 12C:
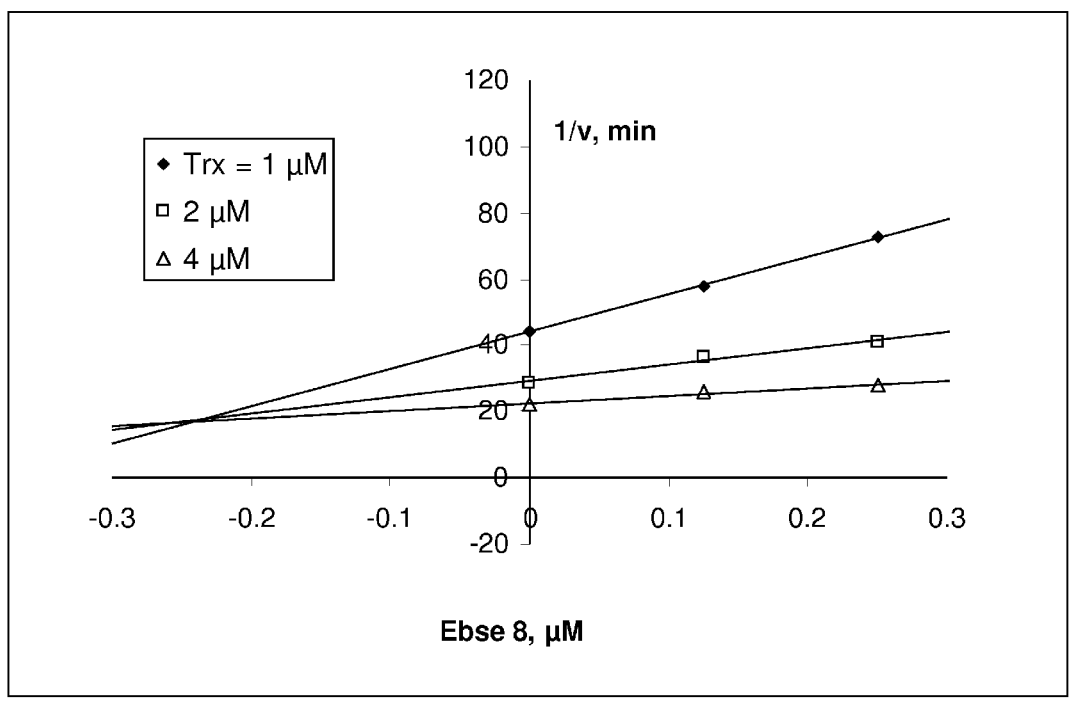
Figure 12D:
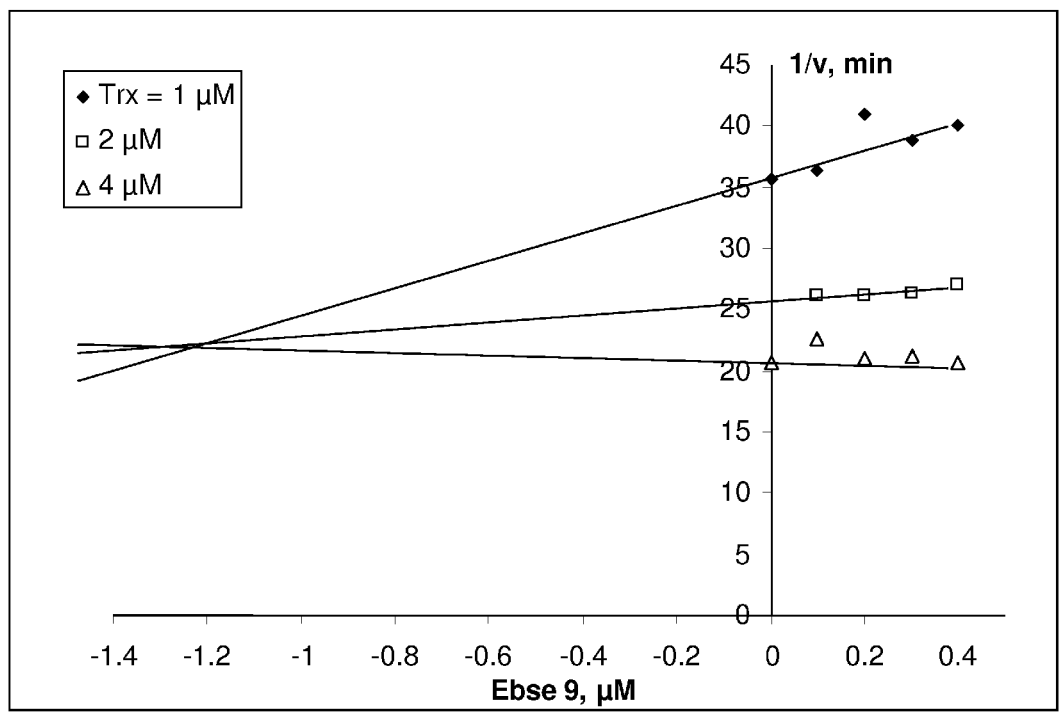
Figure 12E:
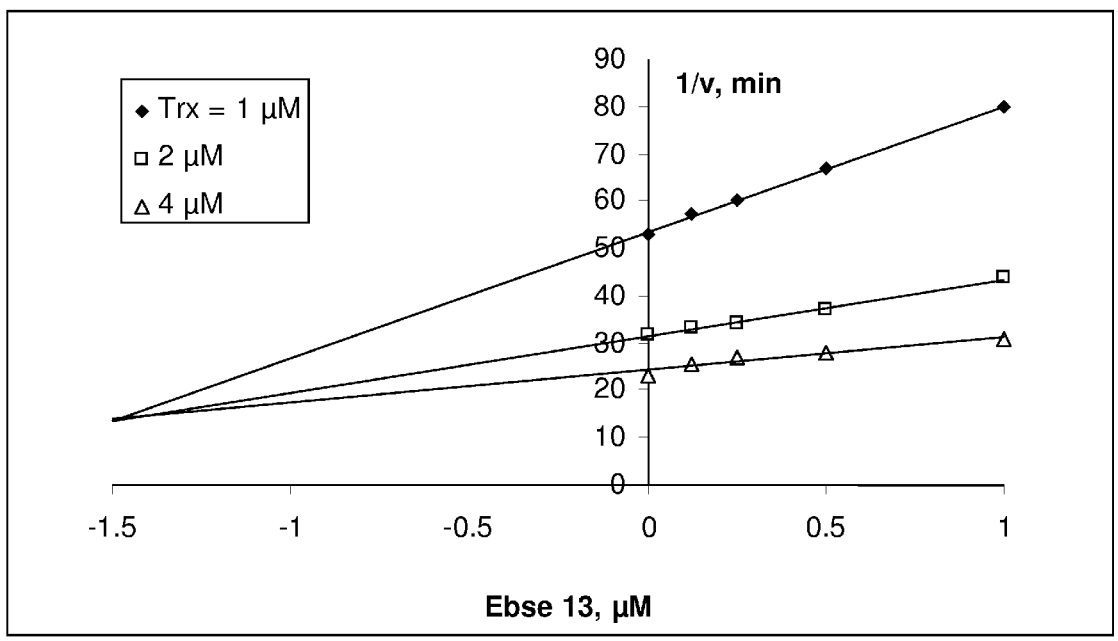
Figure 12F:
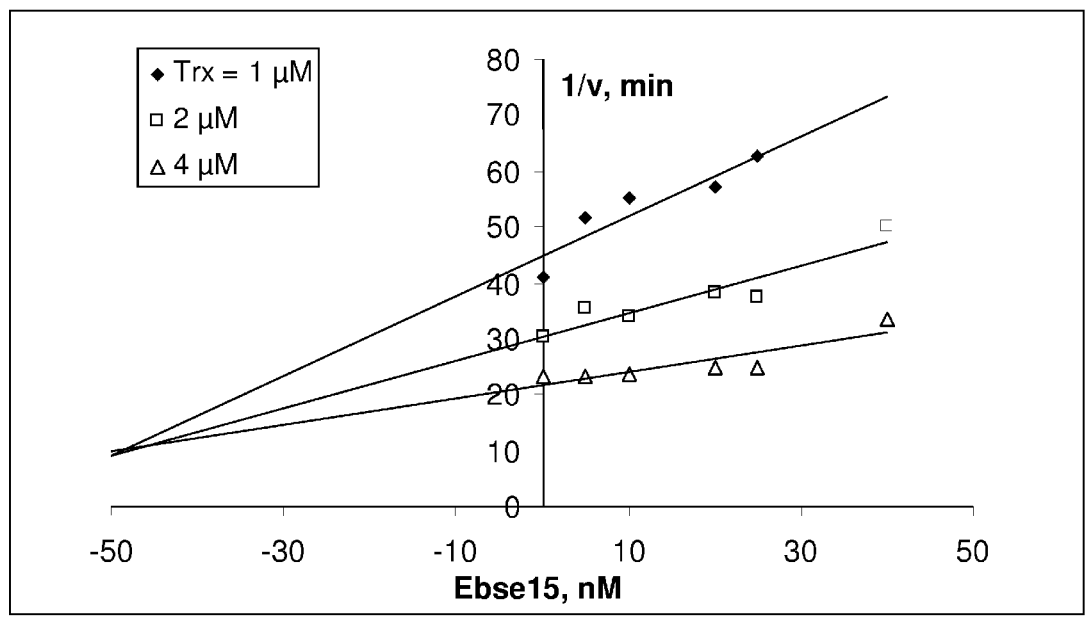

Since ebselen was a potent inhibitor of *E. coli* thioredoxin reductase (FIGS. 3 and 4) we examined whether strains lacking components of the GSH-glutaredoxin reducing pathway (FIG. 1) would be more sensitive to the drug. Thus we examined the sensitivity of gor$^-$ and gshA$^-$ mutants to ebselen, which reside heavily on the TrxR reducing pathway. Wild type bacteria were more resistant than gor$^-$ and gshA$^-$ strains with gor$^-$ and gshA$^-$ strains being the most sensitive (FIGS. 8, 9, 11). This indicates that elimination of parts of the GSH pathway renders cells sensitive to ebselen. The explanation could be that ebselen inhibits TrxR or the thioredoxins, or is eliminated in cells by GSH. The sensitivity of strain trxA$^-$C$^-$ was similar, if not less, than that of the wild type (FIG. 10), suggesting that the two *E. coli* thioredoxins were not primary targets for the compound. However ebselen may be affecting a thioredoxin 1 related function as the gshA$^-$trxA$^-$ strain was more sensitive to the compound. In rich LB liquid cultures, resistance could additionally be associated with GSH from the culture medium which binds and neutralizes ebselen. The sensitivity to ebselen was increased in minimal media where gor$^-$ and gshA$^-$ strains hardly grew in its presence (FIG. 9).

Sensitivity of Pathogenic Bacteria to Ebselen

Glutathione system is lacking and thus thioredoxin system is critical in many bacteria including some important pathogenic bacteria, such as methicillin resistant *Staphylococcus aureus, Helicobacter pylori, Mycobacterium tuberculosis* etc (36-40). Based on our principle that ebselen can target thioredoxin system in glutathione deficient bacteria, ebselen is the potential drug for inhibition of these bacterial. As also shown in reference 10, methicillin resistant *Staphylococcus aureus, Bacillus subtilis* are quite sensitive to ebselen. We also investigated *Mycobacterium tuberculosis* sensitivity on ebselen, the test was done in the radiometric BACTEC 460 system. As shown in Table 3, several multridrug resistant *Mycobacterium tuberculosis* strains are sensitive to ebselen. The medium contains 5 g/l of albumin or 70 µM which will bind ebselen. Ebselen at 10 mg/l is 26 µM. The albumin free SH groups are about 50% or 35 µM. Therefore the MIC is dependent upon albumin saturation and probably lower than 20 mg/l.

We also investigated the inhibition of ebselen on *H. pylori*. For two macrolide sensitive strains, the minimal bactericidal concentration (MBC) are 3.125 and 6.25 µg/ml, for macrolide resistant strains, the MBC is 12.5 µg/ml. Taken together, our results strongly support that the inhibition of ebselen on these glutathione deficient bacteria is due to the oxidization of thioredoxin system by ebselen.

TABLE 3

Sensitivity of MDR *Mycobacterium tuberculosis* to ebselen

| Strain | Ab-res | Sensitivity to ebselen (μg/ml) | | | |
|---|---|---|---|---|---|
| | | 80 | 40 | 20 | 10 |
| H37Rv | S | S | S | S | R |
| Panel3:24 | MDR | S | S | S | R |
| BTB 98-310 | MDR | S | S | S | R |

S: sensitive to rifampicin as positive control (no growth); R: resistant.

TABLE 4

Bactericidal effects of ebselen on *Helicobacter pylori*

| Strain | Sensitivity to Macrolide | Sensitivity to ebselen (μg/ml) | | | | | | | |
|---|---|---|---|---|---|---|---|---|---|
| | | 100 | 50 | 25 | 12.5 | 6.25 | 3.125 | 1.56 | 0.78 |
| MS G6 | S | S | S | S | S | S | S | S | R | R |
| MS G142 | S | S | S | S | S | S | S | R | R | R |
| MR G162 | R | S | S | S | S | S | R | R | R | R |
| MR G193 | R | S | S | S | S | S | R | R | R | R |

S: sensitive; R: resistant.

*E. coli* TrxR Inhibition by Ebselen Derivates

All the benzisoselenazol-3(2H)-one and bisbenzisoselenazol-3(2H)-one derivatives were tested as potential *E. coli* TrxR inhibitors by standard DTNB assay. $IC_{50}$ values were calculated by following the activity of TrxR reducing DTNB by NADPH at 412 nm. The reactions were started by adding 1 mM DTNB to the mixture of 100 nM TrxR, 2 μM Trx, 240 μM NADPH, and different concentration of inhibitor (1-40 μM). For determining the inhibition constants ($K_i$), indicated amount of inhibitor was mixed with total volume 500 μL containing 1 mM DTNB, 240 μM NADPH, fixed thioredoxin concentration (1 or 2 or 4 μM) and buffer containing 50 mM Tris-Cl, 2 mM EDTA, pH 7.5. The reactions were started by adding 6 nM TrxR at room temperature. Inhibition constants ($K_i$) for all the compounds were measured from Dixon plot (FIGS. 12A-12F), which plots 1/v versus [I] (v=$A_{412}$/min, I=Inhibitor concentration, FIGS. 12A-12F). Measured $IC_{50}$ and $K_i$ values (Table 5) indicate that the compounds EbSe 6-9, 12-16 are potent inhibitors for *E. coli* TrxR. The presence of covalent bond between selenium and nitrogen is so important for the biological property of ebselen derivatives. Other derivatives did not show significant inhibition on *E. coli* TrxR.

Oxidation *E. coli* Trx-$(SH)_2$ by Ebselen Derivates

Figure 13:
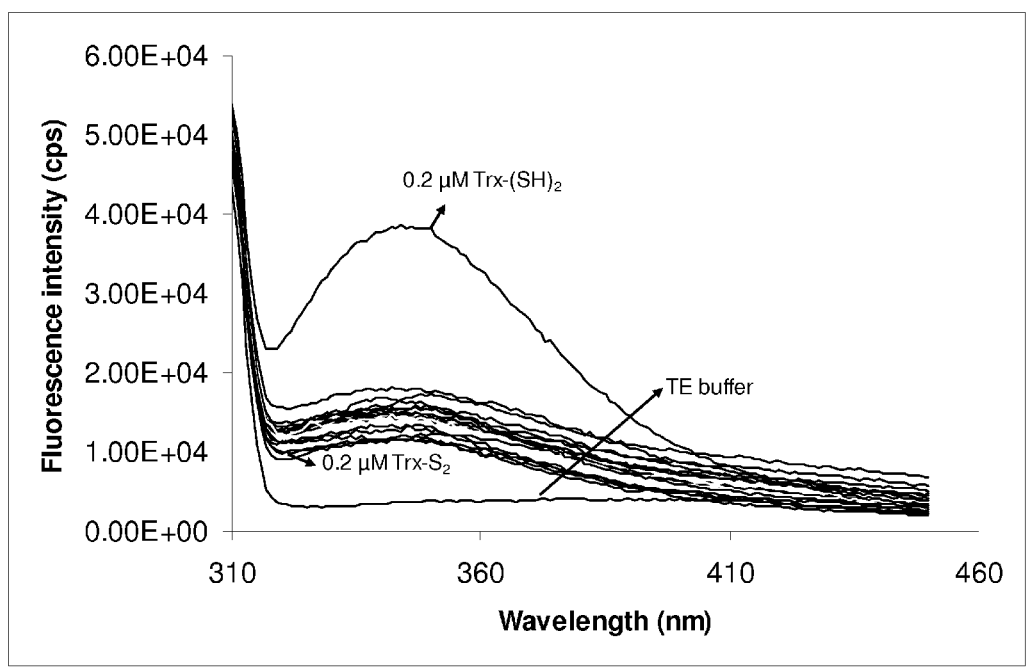
FIG. 13 shows the fluorescence spectra of oxidized and reduced Trx and spectra after the addition of 0.2 μM ebselen and ebselen derivatives in 0.2 μM reduced Trx.

Oxidant property of benzisoselenazol-3(2H)-one derivatives on reduced *E. coli* Trx-$(SH)_2$ were studied by fluorescence spectroscopy. This property was chosen to follow the reaction of Trx with benzisoselenazol-3(2H)-one derivatives since *E. coli* Trx-$(SH)_2$ has 3-fold higher tryptophan fluorescence than Trx-$S_2$. Ebselen is reported as superfast thioredoxin oxidant [32] and hence, used as the reference to compare the oxidant property of other compounds. The change of fluorescence intensity of 0.2 μM Trx-$(SH)_2$ by mixing with 0.2 μM benzisoselenazol-3(2H)-one (FIG. 13) show that they all can oxidize the reduced Trx as the reference compound ebselen under identical conditions.

Correlation Between the Structure and their Inhibition

From the data shown in Table 5, it can be clearly seen that the substitution at nitrogen atom of benzisoselenazol-3(2H)-one ring have significant effect on the inhibition of TrxR. The substitution of benzisoselenazol-3(2H)-one linked by alkyl chains (14-16) has stronger inhibitory effect than unsubstituted (EbSe 6), alkyl (EbSe 2-4), aryl (EbSe 7-10), 2-pyridyl (EbSe 11-12) and 4-pyridyl (EbSe 13) substituted ones. Compounds EbSe 14-16 show similar inhibitory effect irrespective of substitution at the second nitrogen atom and the number of alkyl chains between the two nitrogen atoms. From this observation it seems the second heteroatom nitrogen present in these compounds seems to important characteristic for their strong inhibition. Comparison of EbSe 2-4 show there is no inhibition when hydrogen is substituted by methyl (6) or tert-butyl (7) group. On the other hand comparison of EbSe 6, 12 and 13 indicates that modification of the 2-phenyl-1,2-benzisoselenazol-3(2H)-one into an N-2-pyridyl benzisoselenazol-3(2H)-one or an N-4-pyridyl benzisoselenazol-3 (2H)-one does not have a significant effect. Also inhibition is not much affected by the substitution of phenyl group attached to the nitrogen of benzisoselenazol-3(2H)-one.

Inhibition of Bacterial Growth by Ebselen Derivates

Bacterial TrxR is potent target for antibiotics development, in particular for the bacteria lacking glutathione system. Here *E. coli* DHB4 strains wt, gshA⁻, gor⁻, oxyR⁻ were used as the model to test the antibiotics activity of these ebselen derivates. The MICs of these compounds were list in Table 5. Corresponding to the inhibition capacity of *E. coli* TrxR, ebselen derivates EbSe 6-9 and 13-16 had strong ability to inhibit the bacterial growth. *E. coli* wt strain, strains gshA⁻ or gor⁻ which lost a functional glutathione system show more sensitive to ebselen derivates EbSe 6-9 and 13, suggesting glutathione system play a critical roles in the protection of bacteria from these compound. Whereas, all these strains exhibited the same sensitivity to EbSe 14, 16.

Inhibition of *H. pylori* TrxR and *H. pylori* Strains by PZ-25 (Ebsulfur).

Figure 14:
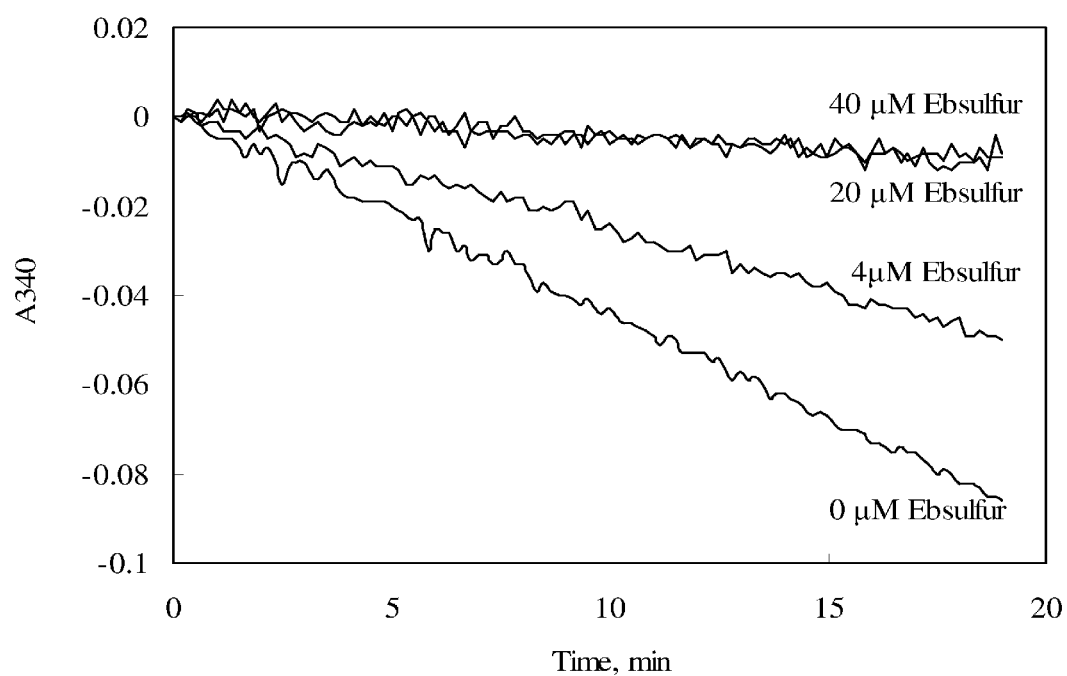
FIG. 14 shows the effect of ebsulfur on the activity by *H. pylori* thioredoxin reductase. *H. pylori* TrxR (100 nM) was incubated with 0, 4, 20, 40 μM of ebsulfur in 0.50 ml semi-microcuvettes containing 0.20 mM NADPH, in 0.10 M Tris-Cl, pH 8.0, 1 mM EDTA and 160 uM insulin. *H. pylori* TrxR activity was followed by insulin reduction after 4 μM of *H. pylori* Trx addition, where a decrease in absorbance at 340 nm represents activity.

*H. pylori* TrxR activity was inhibited by 4, 20, and 40 μM of PZ-25 by insulin reduction assay (FIG. 14). Consistent with the inhibition of *H. pylori* TrxR activity, *H. pylori* strains were shown to be sensitive to ebsulfur. For NCTC11637 strain, the MIC for ebselen, PZ-25, metronidazole was 3.13, 1.56, and 0.78 μg/ml respectively. For strain YS-16, The MIC for ebselen, PZ-25, metronidazole was 3.13, 0.39, 6.25 μg/ml respectively.

Discussion

Ebselen is an antioxidant due to the special selenium chemistry it interplayed with thiol and hydrogen peroxide (1, 3, 24, 32). The mechanism was recently described to be via the mammalian thioredoxin system with the formation of ebselen diselenide as an important part of the mechanism (3, 32). Ebselen also has low toxicity for the human body because the selenium moiety is not liberated during biotransformation so it does not enter the selenium metabolism of the organism (41-43). At low concentrations, ebselen even inhibits a number of enzymes involved in inflammation such as lipoxygenases, NO synthesase, protein kinase C and $H^+/K^+$-ATPase (1). The inhibitions were manifested on the cellular level and may contribute to the anti-inflammatory potential of ebselen (1).

Ebselen has another interesting pharmaceutical profile, namely its antibacterial character, targeting the bacterial thioredoxin reductase as shown herein, with structure and properties distinct from the mammalian counterpart.

The inhibition kinetic parameters determined for the ebselen and its diselenide towards E. coli TrxR indicate that both compounds are strong inhibitors with nanomolar affinities. It was reported that the growth of Staphylococcus aureus 209P was inhibited by 0.20 µg/ml of ebselen, while strains of the family Enterobacteriaceae were more resistant to the drug (10). The selenium in PZ51 was essential, since its sulphur analogue (PZ25) lost the antibacterial activity (10). In results of cell experiments shown in FIGS. 8 and 9, it also clearly showed that ebselen inhibited bacterial strains. The mutants lacking glutathione reductase (gor$^-$) and glutathione (gshA$^-$) showed increased sensitivity.

In E. coli, it was long proposed that thioredoxin system and glutaredoxin system are two crucial pathways for the electron flow to be delivered to the ribonucleotide reductase for DNA synthesis (FIG. 1) (4, 6, 14, 15, 35). Thiol reductions by the two systems also play key roles in cell growth as well as redox regulation of a variety of biological functions. FIG. 8 shows that the sensitivity to ebselen increased with mutants lacking glutathione reductase (gor$^-$) and glutathione (gshA$^-$), indicating that perturbations of the GSH reducing pathway render cells more sensitive to ebselen. The sensitivity to ebselen was increased in minimal media where gor$^-$ and gshA$^-$ strains hardly grew (FIG. 4B). The increased sensitivity in minimal media could be expected since lack of GSH would increase demands for electrons from the thioredoxin system for sulphate reduction (4).

The results clearly show that elimination of GSH or glutathione reductase which makes cells more dependent on the thioredoxin system leads to a greater degree of inhibition. From the results previously published (10) the large difference in sensitivity of bacteria to ebselen is clearly correlated to having GSH or not. Gram positive strains of bacteria like S. aureus or B. subtilis lack GSH (44). Bacillus subtilis e.g. has formally no glutaredoxin pathway but several thioredoxins which are essential (37). The bacterial thioredoxin reductases are therefore drug targets for ebselen.

From a simple chemical point of view, the reaction of Ebselen with the E. coli TrxR is much slower or completely stopped for the reasons of a highly polar CysS-SeEb bond in the second disulphide interchange reaction. E. coli TrxR is known to undergo an essential conformation change allowing electron flows to go through from NADPH to FAD and the active disulphide in each catalytic cycle. The kinetic constant of this conformation change was observed to be ca 53 s$^{-1}$ at 25° C. The inhibition of the E. coli TrxR by ebselen and its diselenide are therefore believed to result from the slow release of ebselen selenol from the relatively polar selenenol-sulphide bridge, and the determined conformation change from FR to FO of the E. coli TrxR-SeEbSe complex.

The E. coli TrxR is known for its high specificity towards its Trx, and in fact, PZ25 and its disulphide are the first two small molecules found as substrates. The specificity of E. coli TrxR as compared with its mammalian counterpart may be principally attributed to this specific conformation change, which differentiates between substrate oxidants except where their disulphide exchange reactions with the active-site thiols in the E. coli TrxR are fast enough to not disrupt the normal conformation change of the enzyme.

The drug has no inhibitory activity of mammalian thioredoxin reductases due to their highly different structures and mechanisms when compared with the ubiquitous bacterial enzymes (8, 18). The ebselen molecule is thus an antioxidant drug with useful antibacterial spectrum and two effects for the price of one.

Thus the non-toxic drug ebselen inhibits bacterial growth due to the large differences in its mechanism of action towards bacterial and mammalian TrxR, the two structurally very distinct enzymes. In pathogenic bacteria like M. tuberculosis the defense from the bacterium against the host killing by reactive oxygen species derived from macrophages is dependent on thioredoxin coupled peroxidises. Thus the inhibition of the thioredoxin system would also sensitize the bacteria in the intracellular environment. Therefore ebselen and derivatives would be effective agents against the survival and virulence of M. tuberculosis in its dormant stage in macrophages where the pathogen has to defend itself against reactive oxygen species from the host as well as to repair its DNA. The latter process is dependent on the thioredoxin system and ribonucleotide reductase and targeted by ebselen. In fact ebselen is also an effective direct inhibitor of E. coli ribonucleotide reductase (data not shown).

In summary, different classes of benzisoselenazol-3(2H)-one substituted compounds were found to exhibit different antibiotic properties because of their inhibition capacity on bacterial thioredoxin reductase. Generally, the N-aryl, N-2-pyridyl and N-4-pyridyl substituted compounds as well as bis-benzisoselenazol-3(2H)-ones possess a good inhibition ability towards bacterial TrxR. But substitution with chloro, carboxy, or nitro groups can alter the antibiotic properties.

The foregoing disclosure of embodiments and exemplary applications of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

TABLE 5

| Compound Number | Structural Formula | IC50 for E. coli TrxR (µM) | $K_i$ for E. coli TrxR (µM) | MIC for wild type DHB4 E. coli (µM) | MIC for gshA$^-$ DHB4 E. coli (µM) | MIC for Gor$^-$ DHB4 E. coli (µM) |
|---|---|---|---|---|---|---|
| EbSe 6 | (structure) | 6 | 0.30 | 40 | 26 | 15 |

TABLE 5-continued

Inhibition constants of ebselen derivates on *E. coli* TrxR, *E. coli* growth

| Compound Number | Structural Formula | IC50 for *E. coli* TrxR (μM) | $K_i$ for *E. coli* TrxR (μM) | MIC for wild type DHB4 *E. coli* (μM) | MIC for gshA⁻ DHB4 *E. coli* (μM) | MIC for Gor⁻ DHB4 *E. coli* (μM) |
|---|---|---|---|---|---|---|
| EbSe 7 | [benzisoselenazol-3(2H)-one with N-(4-chlorophenyl)] | 7 | 0.55 | 34 | 20 | 23 |
| EbSe 8 | [benzisoselenazol-3(2H)-one with N-(4-chloro-2-methylphenyl)] | 6 | 0.25 | 47 | 13 | 24 |
| EbSe 9 | [benzisoselenazol-3(2H)-one with N-(2-carboxyphenyl)] | 7.5 | 1.20 | 49 | 24 | 31 |
| EbSe 10 | [benzisoselenazol-3(2H)-one with N-(4-carboxyphenyl)] | 15 | Not detected | | | |
| EbSe 2 | [benzisoselenazol-3(2H)-one with N—H] | 15 | 1.00 | | | |
| EbSe 3 | [benzisoselenazol-3(2H)-one with N—CH₃] | 15 | Not detected | | | |
| EbSe 4 | [benzisoselenazol-3(2H)-one with N—C(CH₃)₃] | 15 | Not detected | | | |
| EbSe 11 | [benzisoselenazol-3(2H)-one with N-(5-chloropyridin-2-yl)] | >40 | Not detected | No Inhibition | No Inhibition | No Inhibition |
| EbSe 12 | [benzisoselenazol-3(2H)-one with N-(3-nitropyridin-2-yl)] | 3 | 0.25 | No Inhibition | No Inhibition | No Inhibition |

TABLE 5-continued

Inhibition constants of ebselen derivates on *E. coli* TrxR, *E. coli* growth

| Compound Number | Structural Formula | IC50 for E. coli TrxR (μM) | $K_i$ for E. coli TrxR (μM) | MIC for wild type DHB4 E. coli (μM) | MIC for gshA⁻ DHB4 E. coli (μM) | MIC for Gor⁻ DHB4 E. coli (μM) |
|---|---|---|---|---|---|---|
| EbSe 13 | | 3 | 1.5 | 45 | 21 | 24 |
| EbSe 14 | | 2 | 0.05 | 23 | 23 | 19 |
| EbSe 15 | | 2.1 | 0.04 | | | |
| EbSe 16 | | 2.25 | 0.01 | 20 | 20 | 35 |

REFERENCES

1. Schewe, T. (1995) *General Pharmacology* 26, 1153-1169.
2. Ogawa, A., Yoshimoto, T., Kikuchi, H., Sano, K., Saito, I., Yamaguchi, T., Yasuhara, H. & Grp, E. S. (1999) *Cerebrovascular Diseases* 9, 112-118.
3a. patent application Ser. No. 09/926,218, United States Patent and Trademark Office, Arne Holmgren et al, Substrate for thioredoxin reductase, National Stage of PCT JP00/02076.
3b. Zhao, R., Masayasu, H. & Holmgren, A. (2002) *Proc Natl Acad Sci USA* 99, 8579-84.
4. Holmgren, A. (1985) *Annu Rev Biochem* 54, 237-71.
5. Holmgren, A. (1989) *J Biol Chem* 264, 13963-6.
6. Jordan, A. & Reichard, P. (1998) *Annu Rev Biochem* 67, 71-98.
7. Zhong, L., Amer, E. S., Ljung, J., Aslund, F. & Holmgren, A. (1998) *J Biol Chem* 273, 8581-91.
8. Zhong, L. & Holmgren, A. (2000) *J Biol Chem* 275, 18121-8.
9. Williams, C. H., Arscott, L. D., Muller, S., Lennon, B. W., Ludwig, M. L., Wang, P. F., Veine, D. M., Becker, K. & Schirmer, R. H. (2000) *Eur J Biochem* 267, 6110-7.
10. Nozawa, R., Yokota, T. & Fujimoto, T. (1989) *Antimicrob Agents Chemother* 33, 1388-90.
11. Arner, E. S. & Holmgren, A. (2000) *Eur J Biochem* 267, 6102-9.
12. Ritz, D. & Beckwith, J. (2001) *Annu Rev Microbiol* 55, 21-48.
13. Arner, E. S., Zhong, L. & Holmgren, A. (1999) *Methods Enzymol* 300, 226-39.
14. Ortenberg, R., Gon, S., Porat, A. & Beckwith, J. (2004) *Proc Natl Acad Sci USA* 101, 7439-44.
15. Luthman, M. & Holmgren, A. (1982) *Biochemistry* 21, 6628-33.
16. Becker, K., Gromer, S., Schirmer, R. H. & Muller, S. (2000) *Eur J Biochem* 267, 6118-25.
17. Tamura, T. & Stadtman, T. C. (1996) *Proceedings of the National Academy of Sciences of the United States of America* 93, 1006-1011.
18. Zhong, L., Amer, E. S. & Holmgren, A. (2000) *Proc Natl Acad Sci USA* 97, 5854-9.
19. Sandalova, T., Zhong, L., Lindqvist, Y., Holmgren, A. & Schneider, G. (2001) *Proc Natl Acad Sci USA* 98, 9533-8.
20. Lennon, B. W., Williams, C. H., Jr. & Ludwig, M. L. (2000) *Science* 289, 1190-4.
21. Lennon, B. W., Williams, C. H., Jr. & Ludwig, M. L. (1999) *Protein Sci* 8, 2366-79.
22. Waksman, G., Krishna, T. S., Williams, C. H., Jr. & Kuriyan, J. (1994) *J Mol Biol* 236, 800-16.
23. Lennon, B. W. & Williams, C. H., Jr. (1997) *Biochemistry* 36, 9464-77.
24. Sies, H. (1994) *Oxygen Radicals in Biological Systems, Pt D* 234, 476-482.
25. Maulik, N., Yoshida, T. & Das, D. K. (1998) *Free Radic. Biol. Med.* 24, 869-875.
26. Dawson, D. A., Masayasu, H., Graham, D. I. & Macrae, I. M. (1995) *Neurosci. Lett.* 185, 65-69.
27. Takasago, T., Peters, E. E., Graham, D. I., Masayasu, H. & Macrae, I. M. (1997) *Br. J. Pharmacol.* 122, 1251-1256.
28. Imai, H., Masayasu, H., Dewar, D., Graham, D. I. & Macrae, I. M. (2001) *Stroke* 32, 2149-2154.
29. Namura, S., Nagata, I., Takami, S., Masayasu, H. & Kikuchi, H. (2001) *Stroke* 32, 1906-1911.
30. Saito, I., Asano, T., Sano, K., Takakura, K., Abe, H., Yoshimoto, T., Kikuchi, H., Ohta, T. & Ishibashi, S. (1998) *Neurosurgery* 42, 269-278.
31. Yamaguchi, T., Sano, K., Takakura, K., Saito, I., Shinohara, Y., Asano, T. & Yasuhara, H. (1998) *Stroke* 29, 12-17.

32. Zhao, R. & Holmgren, A. (2002) *J Biol Chem* 277, 39456-62.
33. Bien, M., Blaszczyk, B., Kalinowska, K., Mlochowski, J. & Inglot, A. D. (1999) *Arch Immunol Ther Exp (Warsz)* 47, 185-93.
34. Holmgren, A. & Bjornstedt, M. (1995) *Methods Enzymol* 252, 199-208.
35. Prinz, W. A., Aslund, F., Holmgren, A. & Beckwith, J. (1997) *J Biol Chem* 272, 15661-7.
36. Windle, H. J., Fox, A., Ni Eidhin, D. & Kelleher, D. (2000) *J Biol Chem* 275, 5081-9.
37. Scharf, C., Riethdorf, S., Ernst, H., Engelmann, S., Volker, U. & Hecker, M. (1998) *J Bacteriol* 180, 1869-77.
38. Uziel, O., Borovok, I., Schreiber, R., Cohen, G. & Aharonowitz, Y. (2004) *J Bacteriol* 186, 326-34.
39. Comtois, S. L., Gidley, M. D. & Kelly, D. J. (2003) *Microbiology-Sgm* 149, 121-129.
40. Jaeger, T., Budde, H., Flohe, L., Menge, U., Singh, M., Trujillo, M. & Radi, R. (2004) *Archives of Biochemistry and Biophysics* 423, 182-191.
41. Fischer, H., Terlinden, R., Lohr, J. P. & Romer, A. (1988) *Xenobiotica* 18, 1347-1359.
42. Muller, A., Gabriel, H., Sies, H., Terlinden, R., Fischer, H. & Romer, A. (1988) *Biochem. Pharmacol.* 37, 1103-1109.
43. Sies, H. (1989) in *Selenium in Biology and Medicine*, ed. Wendel, A. (Springer-Verlag, Heidelberg), pp. 153-162.
44. Newton, G. L. & Fahey, R. C. (1995) *Methods Enzymol* 251, 148-66.
45. Trujillo, M Mauri, P. L., Benazzi, L., Comini, M., De Palma, A., Flohé, L., Radi, R. Stehr, M., Singh, M. Ursini, F., and Jaeger, T. (2006) J. Biol. Chem. In press on May 8 M601008200.
46. C. H. J. Williams, *In chemistry and biochemistry of flavoenzymes* (F. Müller, Eds, vol 3 pp 121-211. CRC Press Inc. Boca Raton Fla.
47. A.-B. Witte, K. Anestal, E. Jerrelalm, H. Ehrsson, E. S. J. Arnér, *Free Rad. Biol. Med.,* 2005, 39, 696-703.
48. R. Millet, S. Urig, J. Jacob, E. Amtmann, J.-P. Moulinoux, S. Gromer, K. Becker and E. Davioud-Charvet, *J. Med. Chem.,* 2005, 48, 7024-7039.
49. M. P. Rigobello, G. Scutari, A. Folda and A. Bindoli, *Biochem. Pharmacol.,* 2004, 67, 689-696.
50. K. Becker, C. Herold-Mende, J. J. Park, G. Lowe and R. H. Schirmer, *J. Med. Chem.,* 2001, 44, 2784-2792.
51. P. Wipf, S. M. Lynch, G. Powis, A. Birmingham and E. E. Englund, Org. Biomol. Chem., 2005, 3, 3880-3882.
52. P. Wipf, S. M. Lynch, A. Birmingham, G. Tamayo, A. Jiménez, N. Campos and G. Powis, Org. Biomol. Chem., 2004, 2, 1651-1658.
53. P. Wipf, T. D. Hopkins, J.-K. Jung, S. Rodriguez, A. Birmingham, E. C. Southwick, J. S. Lazoc and G. Powis, Biorg. Med. Chem. Lett. 2001, 11, 2637-2641.
54. J. Dessolin, C. Biot and E. Davioud-Charvet, J. Org. Chem., 2001, 66, 5616-5619.
55. K. U. Schallreuter, F. K. Gleason, J. M. Wood, Biochim. Biophys. Acta 1990, 1054, 14-20.
56. S. Gromer, R. H. Schirmer and K. Becker, FEBS Lett. 1997, 412, 318-320.
57. J. Nordberg, L. Zhong, A. Holmgren and E. S. J Amer, J. Biol. Chem., 1998, 273, 10835-10842.
58. L. Engman, I. Cotgreave, M. Angulo, C. W. Taylor, G. D. Paine-Murrieta and G. Powis Anticancer Res., 1997, 17, 4599-4605.
59. L. Engman, T. Kandra, A. Gallegos, R. Williams and G. Powis, Anticancer Drug Des., 2000, 15, 323-330.
60. L. Engman, N. Al-Maharik, M. McNaughton, A. Birmingham and G. Powis, Bioorg. Med. Chem., 2003, 11, 5091-5100.
61. L. Engman, N. Al-Maharik, M. McNaughton, A. Birmingham and G. Powis, Anti-Cancer Drugs 2002, 14, 153-161.
62. H. Wójtowicz, K. Kloc, I. Maliszewska, J. Młochowski, M. Piętka and E. Piasecki, IL FARMACO 2004, 59, 863-868.
63. J. Młochowski, K. Kloc, L. Syper, A. D. Inglot and Piasecki, Liebigs Ann. Chem., 1993, 1239-1244.
64. M. Osajda, K. Kloc, J. Młochowski, E. Piasecki and K. Rybka, Polish J. Chem., 2001, 75, 823-830.
65. D. D. Perrin, W. L. F. Armargo and D. R. Ferrin, Purification of Laboratory Chemicals; Pergamon: New York, 1980.
66. H. J. Windle, A. Fox, D. Ni Eidhin and D. Kelleher, J Biol. Chem. 2000, 275, 5081-9.

Ebse 2

1. Wojtowicz, H.; Kloc, K.; Maliszewska, I.; Mlochowski, J.; Pietka, M.; Piasecki, E. Azaanalogs of ebselen as antimicrobial and antiviral agents: Synthesis and properties. Farmaco (2004), 59(11), 863-868.
2. Mlochowski, Jacek; Brzaszcz, Monika; Chojnacka, Magdalena; Giurg, Miroslaw; Wojtowicz, Halina. Diaryl diselenides and benzisoselenazol-3(2H)-ones as oxygen-transfer agents. ARKIVOC (Gainesville, Fla., United States) (2004), (3), 226-248.
3. Sakimoto, Yukiko; Hirao, Kimihiko; Musaev, Djamaladdin G. Reactivity of Ebtellur Derivatives with the Peroxynitrite Anion: Comparison with their Ebselen Analogues. Journal of Physical Chemistry A (2003), 107(29), 5631-5639.
4. Musaev, Djamaladdin G.; Geletii, Yurii V.; Hill, Craig L.; Hirao, Kimihiko. Can the Ebselen Derivatives Catalyze the Isomerization of Peroxynitrite to Nitrate? Journal of the American Chemical Society (2003), 125(13), 3877-3888.
5. Pfeiffer, W.-D. Product class 21: annulated isoselenazole compounds. Science of Synthesis (2002), 11 931-940.
6. Dakova, B; Walcarius, A; Lamberts, L; Evers, M. Electrochemical behaviour of seleno-organic compounds Part 5. [2H] Benziso-1,2-selenazol-3-one, [3H] benzo-2,1-thiaselenol-3-one and [3H] benzo-1,2-dithiol-3-one. Electrochimica Acta (2001), 46(9), 1259-1265.
7. Xu, Han-Sheng; Hu, Li-Ming; Liu, Zhao-Jie; Peng, Yun-Shan; Guo, Zhen-Qiu. Synthesis of 2-ethoxycarbonylphenylselenoaminomethylphosphonate. Phosphorus, Sulfur and Silicon and the Related Elements (2000), 163 211-218.
8. Mhizha, Sungano; Mlochowski, Jacek. Synthesis of 2-acyl- and 2-sulfonylbenzisoselenazol-3-(2H)-ones. Synthetic Communications (1997), 27(2), 283-291.
9. Bergthaller, Peter; Borst, Hans-Ulrich; Bell, Peter; Buescher, Ralf; Willsau, Johannes; Stetzer, Thomas. Selenium compound as photographic stabilizer. Ger. Offen. (1996), 22 pp.
10. Inglot, Anna D.; Mlochowski, Jacek; Zielinska-Jenczylik, Janina; Piasecki, Egbert; Ledwon, Tomasz K.; Kloc, Krystian. Seleno-organic compounds as immunostimulants: An approach to the structure-activity relationship. Archivum Immunologiae et Therapiae Experimentalis (1996), 44(1), 67-75.
11. Witting, Paul K.; Westerlund, Christer; Stocker, Roland. A rapid and simple screening test for potential inhibitors of tocopherol-mediated peroxidation of LDL lipids. Journal of Lipid Research (1996), 37(4), 853-867.
12. Mlochowski, Jacek; Kloc, Krystian; Syper, Ludwik; Inglot, Anna D.; Piasecki, Egbert. Aromatic and azaromatic diselenides, benzisoselenazolones, and related compounds as immunomodulators active in humans: synthesis and properties. Liebigs Annalen der Chemie (1993), (12), 1239-44.
13. Kuehn-Velten, N.; Sies, H. Optical spectral studies of ebselen interaction with cytochrome P-450 of rat liver microsomes. Biochemical Pharmacology (1989), 38(4), 619-25.
14. Piette, Jean Louis; Loehr, Josef Peter; Leyck, Sigurd. Benzisoselenazolone-containing pharmaceutical preparation and its use. Ger. Offen. (1982), 10 pp.

Ebse 3
1. Musaev, Djamaladdin G.; Geletii, Yurii V.; Hill, Craig L.; Hirao, Kimihiko. Can the Ebselen Derivatives Catalyze the Isomerization of Peroxynitrite to Nitrate? Journal of the American Chemical Society (2003), 125(13), 3877-3888.
2. Pfeiffer, W.-D. Product class 21: annulated isoselenazole compounds. Science of Synthesis (2002), 11 931-940.
3. Inglot, Anna D.; Mlochowski, Jacek; Zielinska-Jenczylik, Janina; Piasecki, Egbert; edwon, Tomasz K.; Kloc, Krystian. Seleno-organic compounds as immunostimulants: An approach to the structure-activity relationship. Archivum Immunologiae et Therapiae Experimentalis (1996), 44(1), 67-75.
4. Mlochowski, Jacek; Giurg, Miroslaw; Kubicz, Elzbieta; Said, Samy B. Benzisoselenazol-3(2H)-ones and bis(2-carbamoylphenyl) diselenides as new catalysts for hydrogen peroxide oxidation of organic compounds. Synthetic Communications (1996), 26(2), 291-300.
5. Piatek, M.; Oleksyn, B.; Sliwinski, J. 2-Methyl-2H-1,2-benzisoselenazol-3-one. Acta Crystallographica, Section C: Crystal Structure Communications (1995), C51(2), 298-301.
6. Mlochowski, Jacek; Kloc, Krystian; Syper, Ludwik; Inglot, Anna D.; Piasecki, Egbert. Aromatic and azaromatic diselenides, benzisoselenazolones, and related compounds as immunomodulators active in humans: synthesis and properties. Liebigs Annalen der Chemie (1993), (12), 1239-44.
7. Mlochowski, J.; Syper, L.; Stefaniak, L.; Domalewski, W.; Schilf, W.; Webb, G. A. A proton, carbon-13, nitrogen-15 and selenium-77 NMR study of three organoselenium compounds. Journal of Molecular Structure (1992), 268(1-3), 311-14.
8. Dakova, B.; Kauffmann, J. M; Evers, M.; Lamberts, L.; Patriarche, G. J. Electrochemical behavior of pharmacologically interesting seleno-organic compounds—I. N-alkyl- and N-aryl-1,2-benzisoselenazol-3(2H)-one, Electrochimica Acta (1990), 35(7), 1133-8.
9. Parnham, M. J.; Biedermann, J.; Bittner, C.; Dereu, N.; Leyck, S.; Wetzig, H. Structure-activity relationships of a series of anti-inflammatory benzisoselenazolones (BISAs). Agents and Actions (1989), 27(3-4), 306-8.
10. Kuehn-Velten, N.; Sies, H. Optical spectral studies of ebselen interaction with cytochrome P-450 of rat liver microsomes. Biochemical Pharmacology (1989), 38(4), 619-25.
11. Welter, Andre; Fischer, Hartmut; Christiaens, Leon; Wendel, Albrecht; Etschenberg, Eugen. 2,2-Diselenobis[benzamide]s of primary amines with glutathione peroxidase-like activity. Ger. Offen. (1986), 26 pp
12. Piette, Jean Louis; Loehr, Josef Peter; Leyck, Sigurd. Benzisoselenazolone-containing pharmaceutical preparation and its use. Ger. Offen. (1982), 10 pp.
13. Van Caneghem, P. Comparative effects of selenium compounds and their sulfur analogs on the stability of lysosomes and mitochondria in vitro. Biochemical Pharmacology (1974), 23(24), 3491-500.

Ebse 4
1. Nakashima, Yusuke; Shimizu, Toshio; Hirabayashi, Kazunori; Kamigata, Nobumasa. Optically Active Seleninamides: Isolation, Absolute Configuration, and Racemization Mechanism. Journal of Organic Chemistry (2005), 70(3), 868-873.
2. Pfeiffer, W.-D. Product class 21: annulated isoselenazole compounds. Science of Synthesis (2002), 11 931-940.
3. Fong, Mei C.; Schiesser, Carl H. Intramolecular Homolytic Substitution with Amidyl Radicals: A Free-Radical Synthesis of Ebselen and Related Analogs. Journal of Organic Chemistry (1997), 62(10), 3103-3108.
4. Bergthaller, Peter; Borst, Hans-Ulrich; Bell, Peter; Buescher, Ralf; Willsau, Johannes; Stetzer, Thomas. Selenium compound as photographic stabilizer. Ger. Offen. (1996), 22 pp.
5. Inglot, Anna D.; Mlochowski, Jacek; Zielinska-Jenczylik, Janina; Piasecki, Egbert; Ledwon, Tomasz K.; Kloc, Krystian. Seleno-organic compounds as immunostimulants: An approach to the structure-activity relationship. Archivum Immunologiae et Therapiae Experimentalis (1996), 44(1), 67-75.
6. Mlochowski, Jacek; Giurg, Miroslaw; Kubicz, Elzbieta; Said, Samy B. Benzisoselenazol-3(2H)-ones and bis(2-carbamoylphenyl) diselenides as new catalysts for hydrogen peroxide oxidation of organic compounds. Synthetic Communications (1996), 26(2), 291-300.
7. Fong, Mei C.; Schiesser, Carl H. Reactions of 2,2'-diselenobis(N-alkylbenzamides) with peroxides: a free-radical synthesis of ebselen and related analogs. Tetrahedron Letters (1995), 36(40), 7329-32.
8. Mlochowski, Jacek; Kloc, Krystian; Syper, Ludwik; Inglot, Anna D.; Piasecki, Egbert. Aromatic and azaromatic diselenides, benzisoselenazolones, and related compounds as immunomodulators active in humans: synthesis and properties. Liebigs Annalen der Chemie (1993), (12), 1239-44.
9. Welter, Andre; Dereu, Norbert. Benzisoselenazolones as antiarthritics. Ger. Offen. (1986), 13 pp.
10. Welter, Andre; Fischer, Hartmut; Christiaens, Leon; Wendel, Albrecht; Etschenberg, Eugen. 2,2-Diselenobis[benzamide]s of primary amines with glutathione peroxidase-like activity. Ger. Offen. (1986), 26 pp.

Ebse 6
This is the parent compound, ebselen and there are a number of reports.

Ebse 7
1. Pfeiffer, W.-D. Product class 21: annulated isoselenazole compounds. Science of Synthesis (2002), 11 931-940
2. Bien, Malgorzata; Blaszczyk, Barbara; Kalinowska, Katarzyna; Mlochowski, Jacek;
3. Inglot, Anna D. Antifungal activity of 2-(4-chlorophenyl)-1,2-benzisoselenazol-3(2H)-one, the analog of Ebselen. Archivum Immunologiae et Therapiae Experimentalis (1999), 47(3), 185-193.
3. Inglot, Anna D.; Mlochowski, Jacek; Zielinska-Jenczylik, Janina; Piasecki, Egbert; Ledwon, Tomasz K.; Kloc, Krystian. Seleno-organic compounds as immunostimulants: An approach to the structure-activity relationship. Archivum Immunologiae et Therapiae Experimentalis (1996), 44(1), 67-75.
4. Blaszczyk, Barbara; Inglot, Anna D.; Kowalczyk-Bronisz, Stefania H.; Szymaniec, Stanislaw; Mlochowski, Jacek. Immunotropic activities of benzisoselenazolones and organic diselenides in mice. Archivum Immunologiae et Therapiae Experimentalis (1995), 43(5-6), 305-11.

5. Mlochowski, Jacek; Kloc, Krystian; Syper, Ludwik; Inglot, Anna D.; Piasecki, Egbert. Aromatic and azaromatic diselenides, benzisoselenazolones, and related compounds as immunomodulators active in humans: synthesis and properties. Liebigs Annalen der Chemie (1993), (12), 1239-44.
6. Dakova, B.; Lamberts, L.; Evers, M.; Dereu, N. Electrochemical behavior of pharmacologically interesting seleno-organic compounds—2. 7-Substituted-N-aryl-1,2-benzisoselenazol-3(2H)-one. Electrochimica Acta (1991), 36(3-4), 631-7.
7. Dakova, B; Kauffmann, J. M; Evers, M.; Lamberts, L; Patriarche, G. J, Electrochemical behavior of pharmacologically interesting seleno-organic compounds—I. N-alkyl- and N-aryl-1,2-benzisoselenazol-3(2H)-one. Electrochimica Acta (1990), 35(7), 1133-8.
8. Kuehn-Velten, Nikolaus; Sies, Helmut. Optical spectral studies of ebselen interaction with cytochrome P-450 of rat liver microsomes. Biochemical Pharmacology (1989), 38(4), 619-25.
9. Kamigata, Nobumasa; Takata, Mayumi; Matsuyama, Haruo; Kobayashi, Michio. Oxidation of thiols and sulfides by 2-aryl-1,2-benzisoselenazol-3(2H)-one 1-oxide. Sulfur Letters (1986), 5(1), 1-7.
10. Welter, Andre; Fischer, Hartmut; Christiaens, Leon; Wendel, Albrecht; Etschenberg, Eugen. 2,2-Diselenobis[benzamide]s of primary amines with glutathione peroxidase-like activity. Ger. Offen. (1986), 26 pp.
11. Dereu, Norbert; Welter, Andre; Wendel, Albrecht; Leyck, Sigurd; Parnham, Michael; Graf, Erich; Sies, Helmut. Glutathione derivatives and pharmaceuticals containing them. Ger. Offen. (1986), 17 pp.
12. Dereu, Norbert; Welter, Andre; Wendel, Albrecht; Leyck, Sigurd; Parnham, Michael; Graf, Erich; Sies, Helmut; Betzing, Hans; Fischer, Hartmut. S-(Carbamoylphenylselenyl) derivatives of glutathione and of aminomercaptocarboxylic acids and pharmaceutical preparations containing them. Eur. Pat. Appl. (1985), 22 pp.
13. Welter, Andre; Christiaens, Leon; Wirtz-Peitz. Benzisoselenazolinones and pharmaceutical preparations containing them. Eur. Pat. Appl. (1982), 30 pp.

Ebse 8
No references known for this exact structure at time of search

Ebse 9
1. Yang, Dongxu; Cheng, Guifang. Effects of seleno-organic compounds as antiinflammatory and antiallergic drugs. Zhongguo Yaoxue Zazhi (Beijing) (1996), 31(8), 470-473.
2. Welter, Andre; Fischer, Hartmut; Christiaens, Leon; Wendel, Albrecht; Etschenberg, Eugen. 2,2-Diselenobis[benzamide]s of primary amines with glutathione peroxidase-like activity. Ger. Offen. (1986), 26 pp.

Ebse 10
1. Liu, Yu; Li, Bin; Li, Li; Zhang, Heng-Yi. Synthesis of organoselenium-modified β-cyclodextrins possessing a 1,2-benzisoselenazol-3(2H)-one moiety and their enzyme-mimic study. Helvetica Chimica Acta (2002), 85(1), 9-18.
2. Mlochowski, Jacek; Gryglewski, Ryszard J.; Inglot, Anna D.; Jakubowsky, Andrzej; Juchniewics, Leszek; Kloc, Krystian. Synthesis and properties of 2-carboxyalkyl-1,2-benzisoselenazol-3(2H)-ones and related organoselenium compounds as nitric oxide synthase inhibitors and cytokine inducers. Liebigs Annalen (1996), (11), 1751-1755.
3. Inglot, Anna D.; Mlochowski, Jacek; Zielinska-Jenczylik, Janina; Piasecki, Egbert; Ledwon, Tomasz K.; Kloc, Krystian. Seleno-organic compounds as immunostimulants: An approach to the structure-activity relationship. Archivum Immunologiae et Therapiae Experimentalis (1996), 44(1), 67-75.
4. Xiao, Ying Xin; Liu, Xiu Fang; Xu, Han Sheng; Sun, Shi Yong; Xu, Bo. Synthesis and anti-lipid peroxidation activity of amino acid derivatives of Ebselen. Chinese Chemical Letters (1994), 5(8), 651-4.
5. Hatchett, R. J.; Gryglewski, R. J.; Mlochowski, J.; Zembowicz, A.; Radziszewski, W. Carboxyebselen, a potent and selective inhibitor of endothelial nitric oxide synthase. Journal of Physiology and Pharmacology (1994), 45(1), 55-67.
6. Mlochowski, Jacek; Kloc, Krystian; Syper, Ludwik; Inglot, Anna D.; Piasecki, Egbert. Aromatic and azaromatic diselenides, benzisoselenazolones, and related compounds as immunomodulators active in humans: synthesis and properties. Liebigs Annalen der Chemie (1993), (12), 1239-44.

Ebse 11
1. Wojtowicz, H.; Kloc, K.; Maliszewska, I.; Mlochowski, J.; Pietka, M.; Piasecki, E. Azaanalogs of ebselen as antimicrobial and antiviral agents: Synthesis and properties. Farmaco (2004), 59(11), 863-868.
2. Wang, Xiaoliang; Gou, Zongru; Lu, Jing; Chu, Fengming; Pan, Yaping; Wang, Ling. The use of benzisoselenazolone compounds against ischemic myocardial damage. PCT Int. Appl. (2003), 77 pp
3. Inglot, Anna D.; Mlochowski, Jacek; Zielinska-Jenczylik, Janina; Piasecki, Egbert; Ledwon, Tomasz K.; Kloc, Krystian. Seleno-organic compounds as immunostimulants: An approach to the structure-activity relationship. Archivum Immunologiae et Therapiae Experimentalis (1996), 44(1), 67-75.
4. Blaszczyk, Barbara; Inglot, Anna D.; Kowalczyk-Bronisz, Stefania H.; Szymaniec, Stanislaw; Mlochowski, Jacek. Immunotropic activities of benzisoselenazolones and organic diselenides in mice. Archivum Immunologiae et Therapiae Exp. (1995), 43(5-6), 305-11.
5. Welter, Andre; Leyck, Sigurd; Etschenberg, Eugen. 1,2-Benzisoselenazolethiones and pharmaceutical preparations containing them. Ger. Offen. (1985), 27 pp.
6. Welter, Andre; Leyck, Sigurd; Etschenberg, Eugen. Benzisoseleniumazolones and pharmaceutical preparations containing them. Ger. Offen. (1984), 26 pp.

Ebse 12
1. Wang, Xiaoliang; Gou, Zongru; Lu, Jing; Chu, Fengming; Pan, Yaping; Wang, Ling. The use of benzisoselenazolone compounds against ischemic myocardial damage. PCT Int. Appl. (2003), 77 pp.

Ebse 13
1. Wang, Xiaoliang; Gou, Zongru; Lu, Jing; Chu, Fengming; Pan, Yaping; Wang, Ling. The use of benzisoselenazolone compounds against ischemic myocardial damage. PCT Int. Appl. (2003), 77 pp.
2. Inglot, Anna D.; Mlochowski, Jacek; Zielinska-Jenczylik, Janina; Piasecki, Egbert; Ledwon, Tomasz K.; Kloc, Krystian. Seleno-organic compounds as immunostimulants: An approach to the structure-activity relationship. Archivum Immunologiae et Therapiae Experimentalis (1996), 44(1), 67-75.
3. Welter, Andre; Leyck, Sigurd; Etschenberg, Eugen. 1,2-Benzisoselenazolethiones and pharmaceutical preparations containing them. Ger. Offen. (1985), 27 pp.
4. Welter, Andre; Leyck, Sigurd; Etschenberg, Eugen. Benzisoseleniumazolones and pharmaceutical preparations containing them. Ger. Offen. (1984), 26 pp.

Ebse 14
1. Shi, Changjin; Yu, Lizhang; Yang, Fengguang; Yan, Jun; Zeng, Huihui. A novel organoselenium compound induces cell cycle arrest and apoptosis in prostate cancer cell lines. Biochemical and Biophysical Research Communications (2003), 309(3), 578-583.
2. Osajda, M.; Kloc, K.; Mlochowski, J.; Piasecki, E.; Rybka, K. Bisbenzisoselenazol-3(2H)-ones, a new group of ebselen analogues. Polish Journal of Chemistry (2001), 75(6), 823-830.
3. Zhao F, Yan J, Deng S, Lan L, He F, Kuang B, Zeng H. A thioredoxin reductase inhibitor induces growth inhibition and apoptosis in five cultured human carcinoma cell lines. Cancer. Lett. 2005 (in press)

Ebse 15
1. Osajda, M.; Kloc, K.; Mlochowski, J.; Piasecki, E.; Rybka, K. Bisbenzisoselenazol-3(2H)-ones, a new group of ebselen analogues. Polish Journal of Chemistry (2001), 75(6), 823-830

Ebse 16
Osajda, M.; Kloc, K.; Mlochowski, J.; Piasecki, E.; Rybka, K. Bisbenzisoselenazol-3(2H)-ones, a new group of ebselen analogues. Polish Journal of Chemistry (2001), 75(6), 823-830

What is claimed is:

1. A method for treating a prokaryotic infection in an animal or human, comprising administering an effective amount of compound PZ 25 or a pharmaceutically acceptable salt thereof to inhibit a prokaryotic thioredoxin reductase, wherein the prokaryotic infection is infection of *Helicobacter pylori*.

2. The method according to claim 1, wherein the animal is a mammal, and wherein the compound is a selective prokaryotic thioredoxin reductase inhibitor which does not substantially inhibit mammalian thioredoxin reductase, administered in an effective amount.

3. The method according to claim 1, further comprising the step of determining a glutathione and glutathione reductase expression of the prokaryote causing the prokaryotic infection and the sensitivity of the prokaryotic thioredoxin reductase to inhibition.

4. A method for treating an animal or human infected with a bacteria lacking glutathione and glutathione reductase, comprising administering an effective amount of compound PZ 25 or a pharmaceutically acceptable salts thereof effective to inhibit a bacterial thioredoxin reductase, wherein the bacteria is *Helicobacter pylori*.

5. A method of treating a mammal infected with a prokaryote, comprising administering at an selective prokaryotic thioredoxin reductase inhibitor which does not inhibit mammalian thioredoxin reductase, in an effective prokaryote thioredoxin reductase inhibitory amount, wherein the selective prokaryotic thioredoxin reductase inhibitor is compound PZ 25 or a pharmaceutically acceptable salt thereof, and wherein the prokaryote is *Helicobacter pylori*.

6. A method of treating a mammal infected with a prokaryotic organism having thioredoxin reductase, comprising administering an effective amount of a prokaryotic thioredoxin reductase inhibitor to treat the infection with the prokaryotic organism, which is a substrate for, but does not substantially inhibit mammalian thioredoxin reductase at said effective amount, wherein the prokaryotic thioredoxin reductase inhibitor is compound PZ 25 or pharmaceutical acceptable salt thereof, and wherein the prokaryotic organism is *Helicobacter pylori*.

* * * * *